United States Patent
Tullman et al.

(10) Patent No.: US 12,275,760 B2
(45) Date of Patent: *Apr. 15, 2025

(54) AMINO ACID-SPECIFIC BINDER AND SELECTIVELY IDENTIFYING AN AMINO ACID

(71) Applicant: Government of the United States of America, as represented by the Secretary of Commerce, Gaithersburg, MD (US)

(72) Inventors: Jennifer A. Tullman, Germantown, MD (US); Zvi Kelman, Gaithersburg, MD (US); John P. Marino, Silver Spring, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 95 days.

This patent is subject to a terminal disclaimer.

(21) Appl. No.: 17/837,082

(22) Filed: Jun. 10, 2022

(65) Prior Publication Data

US 2022/0315628 A1    Oct. 6, 2022

Related U.S. Application Data

(60) Continuation of application No. 16/986,334, filed on Aug. 6, 2020, now Pat. No. 11,390,653, which is a division of application No. 16/395,407, filed on Apr. 26, 2019, now Pat. No. 10,836,798.

(60) Provisional application No. 62/757,271, filed on Nov. 8, 2018.

(51) Int. Cl.
C07K 14/195    (2006.01)
C07K 1/13      (2006.01)
G01N 33/58     (2006.01)

(52) U.S. Cl.
CPC .............. *C07K 14/195* (2013.01); *C07K 1/13* (2013.01); *G01N 33/582* (2013.01)

(58) Field of Classification Search
None
See application file for complete search history.

(56) References Cited

U.S. PATENT DOCUMENTS 9,566,335 B1    2/2017  Emili et al.
11,390,653 B2*  7/2022  Tullman ............. G01N 33/6818

FOREIGN PATENT DOCUMENTS

WO    2019089836 A1    5/2019

OTHER PUBLICATIONS

Stein, B., et al., "Structural Basis of an N-Degron Adaptor with More Stringent Specificity", Structure, 2016, 0.232-242, vol. 24.
GenBank AAK24438 (Year:2001).
NCBI Reference Sequence WO_010917259 (Year:2019).
GenBank EWC87102.1 (Year:2014).
NCBI Reference Sequence NP_355189 (Year:2016).

* cited by examiner

*Primary Examiner* — Sudhakar Katakam
*Assistant Examiner* — Zachary J Miknis
(74) *Attorney, Agent, or Firm* — Office of Chief Counsel for National Institute of Standards and Technology

(57) ABSTRACT

An amino acid-specific binder selectively binds to a binding amino acid. A binder complex selectively identifies the binding amino acid and includes an adjunct attached to the amino acid-specific binder. The adjunct includes a taggant, protein, substrate, or chemical modifier. Selectively identifying an N-terminal amino acid includes anchoring a C-terminal end; contacting an N-terminal amino acid of the anchored analyte with the binder complex; selectively binding when the N-terminal amino acid includes the binding amino acid; producing, by the taggant of the tagged complex, a taggant signal; detecting the taggant signal; and identifying the N-terminal amino acid based on the taggant signal.

17 Claims, 21 Drawing Sheets

Specification includes a Sequence Listing.

(A)

(B)

(A) <u>228</u>

236   200

(B) <u>228</u>

236   246   200

(A) 228

214    200

(B) 228

238    200

(C) 228

242    200

(D) 228

200

240

(A) 228

200A  200B  236

(B) 228

(C) 228

(A) 212  (B) 212  (C) 212

(D) 212, 248, 250

(E) 212, 248, 250

(A)  226

(B)  226

(A)

Remove 209A (B)

(C)

(D)

```
AtumClpS2     1 ...........SDSPVDLKPKPKVKPKLERPKLYKVML
PfalClpS     73 NLEKIKKLRNVIKEIKKDNIKEADEHEKKEREKETSAWKVIL ◄

AtumClpS2       ..LNDDYTPREFVT.VLKAVFRMSEDTGRRVMTAHRFGSAVV
PfalClpS        YNDDIHNFTYVTDVIVKVGQISKAKAHTITVEAHSTGQALI
                  ▲▲▲        ▲

AtumClpS2       VVCERDIAETKAKATDLGKEAGEPLMFTTEPEE......102
PfalClpS        LSTWKSKAEKYCQELQQN.....GLTVSIIHESQLKDKQKK 192
                  ▲▲   ▲▲
```

Figure 19

SEQUENCE LISTING

<160> NUMBER OF SEQ ID NOS: 27

<210> SEQ ID NO 1
<211> LENGTH: 102
<212> TYPE: PRT
<213> ORGANISM: Escherichia coli

<400> SEQUENCE: 1

Ser Asp Ser Pro Val Asp Leu Lys Pro Lys Pro Lys Val Lys Pro Lys
1               5                   10                  15

Leu Glu Arg Pro Lys Leu Tyr Lys Val Met Leu Leu Asn Asp Asp Tyr
                20                  25                  30

Thr Cys Pro Ser Phe Val Thr Val Leu Lys Ala Val Phe Arg Met
            35                  40                  45

Ser Glu Asp Thr Gly Arg Arg Val Met Met Thr Ala His Arg Phe Gly
        50                  55                  60

Ser Ala Val Val Val Cys Glu Arg Asp Ile Ala Glu Thr Lys Ala
65                  70                  75                  80

Lys Glu Ala Thr Asp Leu Gly Lys Glu Ala Gly Phe Pro Leu Met Phe
                85                  90                  95

Thr Thr Glu Pro Glu Glu
            100

<210> SEQ ID NO 2
<211> LENGTH: 102
<212> TYPE: PRT
<213> ORGANISM: Escherichia coli

<400> SEQUENCE: 2

Ser Asp Ser Pro Val Asp Leu Lys Pro Lys Pro Lys Val Lys Pro Lys
1               5                   10                  15

Leu Glu Arg Pro Lys Leu Tyr Lys Val Met Leu Leu Asn Asp Asp Tyr
                20                  25                  30

Thr Cys Ser Trp Phe Val Thr Val Leu Lys Ala Val Phe Arg Met
            35                  40                  45

Ser Glu Asp Thr Gly Arg Arg Val Met Met Thr Ala His Arg Phe Gly
        50                  55                  60

Ser Ala Val Val Val Cys Glu Arg Asp Ile Ala Glu Thr Lys Ala
65                  70                  75                  80

Lys Glu Ala Thr Asp Leu Gly Lys Glu Ala Gly Phe Pro Leu Met Phe
                85                  90                  95

Thr Thr Glu Pro Glu Glu
            100

<210> SEQ ID NO 3
<211> LENGTH: 102
<212> TYPE: PRT
<213> ORGANISM: Escherichia coli

<400> SEQUENCE: 3

Ser Asp Ser Pro Val Asp Leu Lys Pro Lys Pro Lys Val Lys Pro Lys
1               5                   10                  15

Leu Glu Arg Pro Lys Leu Tyr Lys Val Met Leu Leu Asn Asp Asp Tyr
                20                  25                  30

Thr Pro Met Ser Phe Val Thr Val Leu Lys Ala Val Phe Arg Met
            35                  40                  45

Ser Glu Asp Thr Gly Arg Arg Val Met Met Thr Ala His Arg Phe Gly
        50                  55                  60

Ser Ala Val Val Val Cys Glu Arg Asp Ile Ala Glu Thr Lys Ala
65                  70                  75                  80

Lys Glu Ala Thr Asp Leu Gly Lys Glu Ala Gly Phe Pro Leu Met Phe
                85                  90                  95

```
Thr Thr Glu Pro Glu Glu
            100

<210> SEQ ID NO 4
<211> LENGTH: 102
<212> TYPE: PRT
<213> ORGANISM: Escherichia coli

<400> SEQUENCE: 4

Ser Asp Ser Pro Val Asp Leu Lys Pro Lys Pro Lys Val Lys Pro Lys
1               5                   10                  15

Leu Glu Arg Pro Lys Leu Tyr Lys Val Met Leu Leu Asn Asp Asp Tyr
            20                  25                  30

Thr Ser Gly Arg Phe Val Thr Val Leu Lys Ala Val Phe Arg Met
        35                  40                  45

Ser Glu Asp Thr Gly Arg Arg Val Met Met Thr Ala His Arg Phe Gly
    50                  55                  60

Ser Ala Val Val Val Cys Glu Arg Asp Ile Ala Glu Thr Lys Ala
65                  70                  75                  80

Lys Glu Ala Thr Asp Leu Gly Lys Glu Ala Gly Phe Pro Leu Met Phe
                85                  90                  95

Thr Thr Glu Pro Glu Glu
            100

<210> SEQ ID NO 5
<211> LENGTH: 102
<212> TYPE: PRT
<213> ORGANISM: Escherichia coli

<400> SEQUENCE: 5

Ser Asp Ser Pro Val Asp Leu Lys Pro Lys Pro Lys Val Lys Pro Lys
1               5                   10                  15

Leu Glu Arg Pro Lys Leu Tyr Lys Val Met Leu Leu Asn Asp Asp Tyr
            20                  25                  30

Thr Pro Met Pro Phe Val Thr Val Leu Lys Ala Val Phe Arg Met
        35                  40                  45

Ser Glu Asp Thr Gly Arg Arg Val Met Met Thr Ala His Arg Phe Gly
    50                  55                  60

Ser Ala Val Val Val Cys Glu Arg Asp Ile Ala Glu Thr Lys Ala
65                  70                  75                  80

Lys Glu Ala Thr Asp Leu Gly Lys Glu Ala Gly Phe Pro Leu Met Phe
                85                  90                  95

Thr Thr Glu Pro Glu Glu
            100

<210> SEQ ID NO 6
<211> LENGTH: 102
<212> TYPE: PRT
<213> ORGANISM: Escherichia coli

<400> SEQUENCE: 6

Ser Asp Ser Pro Val Asp Leu Lys Pro Lys Pro Lys Val Lys Pro Lys
1               5                   10                  15

Leu Glu Arg Pro Lys Leu Tyr Lys Val Met Leu Leu Asn Asp Asp Tyr
            20                  25                  30

Thr Pro Arg Glu Phe Val Thr Val Leu Lys Ala Val Phe Arg Met
        35                  40                  45

Ser Glu Asp Thr Gly Arg Arg Val Met Met Thr Ala His Arg Phe Gly
```

```
                    50                  55                  60
Ser Ala Val Val Val Ser Glu Arg Asp Ile Ala Glu Thr Lys Ala
 65                  70                  75                  80

Lys Glu Ala Thr Asp Leu Gly Lys Glu Ala Gly Phe Pro Leu Met Phe
                 85                  90                  95

Thr Thr Glu Pro Glu Glu
            100

<210> SEQ ID NO 7
<211> LENGTH: 102
<212> TYPE: PRT
<213> ORGANISM: Escherichia coli

<400> SEQUENCE: 7

Ser Asp Ser Pro Val Asp Leu Lys Pro Lys Pro Lys Val Lys Pro Lys
 1               5                  10                  15

Leu Glu Arg Pro Lys Leu Tyr Lys Val Met Leu Leu Asn Asp Asp Tyr
                20                  25                  30

Thr Pro Arg Glu Phe Val Thr Val Leu Lys Ala Val Phe Arg Met
             35                  40                  45

Ser Glu Asp Thr Gly Arg Arg Val Met Met Thr Ala His Arg Phe Gly
         50                  55                  60

Ser Ala Val Val Val Ser Glu Arg Asp Ile Ala Glu Thr Lys Ala
 65                  70                  75                  80

Lys Glu Ala Thr Asp Leu Gly Lys Glu Ala Gly Phe Pro Leu Met Phe
                 85                  90                  95

Thr Thr Glu Pro Glu Glu
            100

<210> SEQ ID NO 8
<211> LENGTH: 102
<212> TYPE: PRT
<213> ORGANISM: Escherichia coli

<400> SEQUENCE: 8

Ser Asp Ser Pro Val Asp Leu Lys Pro Lys Pro Lys Val Lys Pro Lys
 1               5                  10                  15

Leu Glu Arg Pro Lys Leu Tyr Lys Val Met Leu Leu Asn Asp Asp Tyr
                20                  25                  30

Thr Pro Met Ser Phe Val Thr Glu Val Leu Lys Ala Val Phe Asn Met
             35                  40                  45

Ser Glu Asp Gln Gly Arg Arg Val Met Met Thr Ala His Arg Phe Gly
         50                  55                  60

Ser Ala Val Val Gly Val Ser Thr Arg Asp Ile Ala Glu Thr Lys Ala
 65                  70                  75                  80

Lys Gln Ala Thr Asp Leu Ala Arg Glu Ala Gly Phe Pro Leu Met Phe
                 85                  90                  95

Thr Thr Glu Pro Glu Glu
            100

<210> SEQ ID NO 9
<211> LENGTH: 82
<212> TYPE: PRT
<213> ORGANISM: Escherichia coli

<400> SEQUENCE: 9

Pro Ser Leu Tyr Arg Val Leu Ile Leu Asn Asp Asp Tyr Thr Pro Met
 1               5                  10                  15
```

```
Glu Phe Val Val Tyr Val Leu Glu Arg Phe Phe Asn Lys Ser Arg Glu
            20                  25                  30

Asp Ala Thr Arg Ile Met Leu His Val His Gln Asn Gly Val Gly Val
        35                  40                  45

Cys Gly Val Tyr Thr Tyr Glu Val Ala Glu Thr Lys Val Ala Gln Val
    50                  55                  60

Ile Asp Ser Ala Arg Arg His Gln His Pro Leu Gln Cys Thr Met Glu
65                  70                  75                  80

Lys Asp

<210> SEQ ID NO 10
<211> LENGTH: 120
<212> TYPE: PRT
<213> ORGANISM: Escherichia coli

<400> SEQUENCE: 10

Asn Leu Glu Lys Ile Lys Lys Leu Arg Asn Val Ile Lys Glu Ile Lys
1               5                   10                  15

Lys Asp Asn Ile Lys Glu Ala Asp Glu His Glu Lys Lys Glu Arg Glu
            20                  25                  30

Lys Glu Thr Ser Ala Trp Lys Val Ile Leu Tyr Asn Asp Asp Ile His
        35                  40                  45

Lys Phe Ser Tyr Val Thr Asp Val Ile Val Lys Val Val Gly Gln Ile
    50                  55                  60

Ser Lys Ala Lys Ala His Thr Ile Thr Val Glu Ala His Ser Thr Gly
65                  70                  75                  80

Gln Ala Leu Ile Leu Ser Thr Trp Lys Ser Lys Ala Glu Lys Tyr Cys
                85                  90                  95

Gln Glu Leu Gln Gln Asn Gly Leu Thr Val Ser Ile Ile His Glu Ser
            100                 105                 110

Gln Leu Lys Asp Lys Gln Lys Lys
        115                 120

<210> SEQ ID NO 11
<211> LENGTH: 69
<212> TYPE: PRT
<213> ORGANISM: Agrobacterium tumefaciens

<400> SEQUENCE: 11

Ser Asp Ser Pro Val Asp Leu Lys Pro Lys Pro Lys Val Lys Pro Lys
1               5                   10                  15

Leu Glu Arg Pro Lys Leu Tyr Lys Val Met Leu Asn Leu Glu Lys Ile
            20                  25                  30

Lys Lys Leu Arg Asn Val Ile Lys Glu Ile Lys Lys Asp Asn Ile Lys
        35                  40                  45

Glu Ala Asp Glu His Glu Lys Lys Glu Arg Glu Lys Glu Thr Ser Ala
    50                  55                  60

Trp Lys Val Ile Leu
65

<210> SEQ ID NO 12
<211> LENGTH: 83
<212> TYPE: PRT
<213> ORGANISM: Plasmodium falciparum

<400> SEQUENCE: 12

Leu Asn Asp Asp Tyr Thr Pro Arg Glu Phe Val Thr Val Val Leu Lys
```

```
                1               5                   10                  15
            Ala Val Phe Arg Met Ser Glu Asp Thr Gly Arg Arg Val Met Met Thr
                            20                  25                  30
            Ala His Arg Phe Gly Ser Ala Val Val Thr Asn Asp Asp Ile His Asn
                        35                  40                  45
            Phe Thr Tyr Val Thr Asp Val Ile Val Lys Val Val Gly Gln Ile Ser
                    50                  55                  60
            Lys Ala Lys Ala His Thr Ile Thr Val Glu Ala His Ser Thr Gly Gln
            65                  70                  75                  80

Ser Leu Ile

<210> SEQ ID NO 13
<211> LENGTH: 15
<212> TYPE: PRT
<213> ORGANISM: Escherichia coli

<400> SEQUENCE: 13

Met Gly His His His His His His Glu Asn Leu Tyr Phe Gln Gly
1               5                   10                  15

<210> SEQ ID NO 14
<211> LENGTH: 5
<212> TYPE: PRT
<213> ORGANISM: Escherichia coli

<400> SEQUENCE: 14

Gly Gly Gly Gly Ser
1               5

<210> SEQ ID NO 15
<211> LENGTH: 21
<212> TYPE: PRT
<213> ORGANISM: Escherichia coli

<400> SEQUENCE: 15

Cys Cys Ala Thr Ala Cys Gly Ala Cys Gly Thr Thr Cys Cys Ala Gly
1               5                   10                  15

Ala Cys Thr Ala Cys
                20

<210> SEQ ID NO 16
<211> LENGTH: 20
<212> TYPE: PRT
<213> ORGANISM: Escherichia coli

<400> SEQUENCE: 16

Thr Ala Ala Thr Ala Cys Gly Ala Cys Thr Cys Ala Cys Thr Ala Thr
1               5                   10                  15

Ala Gly Gly Gly
            20

<210> SEQ ID NO 17
<211> LENGTH: 89
<212> TYPE: PRT
<213> ORGANISM: Escherichia coli

<400> SEQUENCE: 17

Thr Ala Ala Gly Cys Thr Cys Thr Ala Cys Ala Ala Gly Gly Thr Cys
1               5                   10                  15

Ala Thr Gly Cys Thr Gly Cys Thr Gly Ala Ala Thr Gly Ala Cys Gly
            20                  25                  30
```

```
Ala Cys Thr Ala Thr Ala Cys Gly Asn Asn Lys Asn Lys Asn Asn
            35                  40                  45

Lys Thr Thr Thr Gly Thr Cys Ala Cys Cys Gly Gly Thr Gly Thr Gly
     50                  55                  60

Cys Thr Gly Ala Ala Gly Gly Cys Cys Gly Thr Cys Thr Thr Thr Cys
 65              70                  75                  80

Gly Cys Ala Thr Gly Ala Gly Cys Gly
                85
```

```
<210> SEQ ID NO 18
<211> LENGTH: 6
<212> TYPE: PRT
<213> ORGANISM: Escherichia coli
<220> FEATURE:
<221> NAME/KEY: misc_feature
<222> LOCATION: (1)..(1)
<223> OTHER INFORMATION: Xaa can be any naturally occurring amino acid

<400> SEQUENCE: 18

Xaa Asp Glu Asp Leu Glu
1               5
```

```
<210> SEQ ID NO 19
<211> LENGTH: 6
<212> TYPE: PRT
<213> ORGANISM: Escherichia coli
<220> FEATURE:
<221> NAME/KEY: misc_feature
<222> LOCATION: (1)..(1)
<223> OTHER INFORMATION: Xaa can be any naturally occurring amino acid

<400> SEQUENCE: 19

Xaa Gly Val Glu Cys Lys
1               5
```

```
<210> SEQ ID NO 20
<211> LENGTH: 33
<212> TYPE: PRT
<213> ORGANISM: Escherichia coli

<400> SEQUENCE: 20

Ser Asp Ser Pro Val Asp Leu Lys Pro Lys Pro Lys Val Lys Pro Lys
1               5                   10                  15

Leu Glu Arg Pro Lys Leu Tyr Lys Val Met Leu Leu Asn Asp Asp Tyr
            20                  25                  30

Thr
```

```
<210> SEQ ID NO 21
<211> LENGTH: 33
<212> TYPE: PRT
<213> ORGANISM: Escherichia coli

<400> SEQUENCE: 21

Ser Asp Ser Pro Val Asp Leu Lys Pro Lys Pro Lys Val Lys Pro Lys
1               5                   10                  15

Leu Glu Arg Pro Lys Leu Tyr Lys Val Met Leu Leu Asn Asp Asp Tyr
            20                  25                  30

Thr
```

```
<210> SEQ ID NO 22
<211> LENGTH: 6
<212> TYPE: PRT
```

```
<213> ORGANISM: Escherichia coli

<400> SEQUENCE: 22

Val Leu Lys Ala Val Phe
1               5

<210> SEQ ID NO 23
<211> LENGTH: 4
<212> TYPE: PRT
<213> ORGANISM: Escherichia coli

<400> SEQUENCE: 23

Met Ser Glu Asp
1

<210> SEQ ID NO 24
<211> LENGTH: 18
<212> TYPE: PRT
<213> ORGANISM: Escherichia coli

<400> SEQUENCE: 24

Gly Arg Arg Val Met Met Thr Ala His Arg Phe Gly Ser Ala Val Val
1               5                   10                  15

Val Val

<210> SEQ ID NO 25
<211> LENGTH: 9
<212> TYPE: PRT
<213> ORGANISM: Escherichia coli

<400> SEQUENCE: 25

Arg Asp Ile Ala Glu Thr Lys Ala Lys
1               5

<210> SEQ ID NO 26
<211> LENGTH: 4
<212> TYPE: PRT
<213> ORGANISM: Escherichia coli

<400> SEQUENCE: 26

Ala Thr Asp Leu
1

<210> SEQ ID NO 27
<211> LENGTH: 14
<212> TYPE: PRT
<213> ORGANISM: Escherichia coli

<400> SEQUENCE: 27

Glu Ala Gly Phe Pro Leu Met Phe Thr Thr Glu Pro Glu Glu
1               5                   10
```

AMINO ACID-SPECIFIC BINDER AND SELECTIVELY IDENTIFYING AN AMINO ACID

CROSS REFERENCE TO RELATED APPLICATIONS

This application is a continuation of U.S. patent application Ser. No. 16/986,334, filed Aug. 6, 2020, which is a divisional of U.S. patent application Ser. No. 16/395,407, filed Apr. 26, 2019, now U.S. Pat. No. 10,836,798, which claims benefit of U.S. Provisional Patent Application Ser. No. 62/757,271, filed Nov. 8, 2018, the disclosures of which are incorporated herein by reference in their entireties.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention. Licensing inquiries may be directed to the Technology Partnerships Office, NIST, Gaithersburg, Md., 20899; voice 301-975-2573; email tpo@nist.gov; reference NIST Docket Number 18-066D1C1.

SEQUENCE LISTING

This application contains a Sequence Listing. CD-ROM discs Copy 1 and Copy 2 are identical, contain a copy of the Sequence Listing under 37 CFR Section 1.821 (e), and are read-only memory computer-readable compact discs. Each CD-ROM disc contains a copy of the Sequence Listing in ASCII text format. The Sequence Listing is named "18-066D1C1_Sequence Listing_ST25.txt." The copies of the Sequence Listing on the CD-ROM discs are hereby incorporated by reference in their entirety.

BRIEF DESCRIPTION

Disclosed is an amino acid-specific binder for selectively binding to an amino acid in an analyte, the amino acid-specific binder comprising: a first amino acid sequence comprising

```
a first amino acid sequence comprising
                                     (Sequence ID No. 1)
SDSPVDLKPKPKVKPKLERPKLYKVMLLNDDYTCPSFVTVVLKAVFRMS
EDTGRRVMMTAHRFGSAVVVVCERDIAETKAKEATDLGKEAGFPLMFTT
EPEE;

a second amino acid sequence comprising
                                     (Sequence ID No. 2)
SDSPVDLKPKPKVKPKLERPKLYKVMLLNDDYTCSWFVTVVLKAVFRMS
EDTGRRVMMTAHRFGSAVVVVCERDIAETKAKEATDLGKEAGFPLMFTT
EPEE;

a third amino acid sequence comprising
                                     (Sequence ID No. 3)
SDSPVDLKPKPKVKPKLERPKLYKVMLLNDDYTPMSFVTVVLKAVFRMS
EDTGRRVMMTAHRFGSAVVVVCERDIAETKAKEATDLGKEAGFPLMFTT
EPEE;

A fourth amino acid sequence comprising
                                     (Sequence ID No. 4)
SDSPVDLKPKPKVKPKLERPKLYKVMLLNDDYTSGRFVTVVLKAVFRMS
EDTGRRVMMTAHRFGSAVVVVCERDIAETKAKEATDLGKEAGFPLMFTT
EPEE;

a fifth amino acid sequence comprising
                                     (Sequence ID No. 5)
SDSPVDLKPKPKVKPKLERPKLYKVMLLNDDYTPMPFVTVVLKAVFRMS
EDTGRRVMMTAHRFGSAVVVVCERDIAETKAKEATDLGKEAGFPLMFTT
EPEE;

a sixth amino acid sequence comprising
                                     (Sequence ID No. 6)
SDSPVDLKPKPKVKPKLERPKLYKVMLLNDDYTPREFVTVVLKAVFRMS
EDTGRRVMMTAHRFGSAVVVVSERDIAETKAKEATDLGKEAGFPLMFTT
EPEE;

a seventh amino acid sequence comprising
                                     (Sequence ID No. 7)
SDSPVDLKPKPKVKPKLERPKLYKVMLLNDDYTPREFVTEVLKAVFNMS
EDQGRRVMMTAHRFGSAVVGVCTRDIAETKAKQATDLAREAGFPLMFTT
EPEE;

an eighth amino acid sequence comprising
                                     (Sequence ID No. 8)
SDSPVDLKPKPKVKPKLERPKLYKVMLLNDDYTPMSFVTEVLKAVFNMS
EDQGRRVMMTAHRFGSAVVGVSTRDIAETKAKQATDLAREAGFPLMFTT
EPEE;

a ninth amino acid sequence comprising
                                     (Sequence ID No. 9)
PSLYRVLILNDDYTPMEFVVYVLERFFNKSREDATRIMLHVHQNGVGVC
GVYTYEVAETKVAQVIDSARRHQHPLQCTMEKD;

a tenth amino acid sequence comprising; or
                                     (Sequence ID No. 10)
NLEKIKKLRNVIKEIKKDNIKEADEHEKKEREKETSAWKVILYNDDIHK
FSYVTDVIVKVVGQISKAKAHTITVEAHSTGQALILSTWKSKAEKYCQE
LQQNGLTVSIIHESQLKDKQKK.
```

Disclosed is an amino acid-specific binder for selectively binding to an amino acid in an analyte, the amino acid-specific binder comprising an amino acid sequence with a homology of at least 30% compared to an amino acid sequence comprising:

```
a first amino acid sequence comprising
                                     (Sequence ID No. 1)
SDSPVDLKPKPKVKPKLERPKLYKVMLLNDDYTCPSFVTVVLKAVFRMS
EDTGRRVMMTAHRFGSAVVVVCERDIAETKAKEATDLGKEAGFPLMFTT
EPEE;

a second amino acid sequence comprising
                                     (Sequence ID No. 2)
SDSPVDLKPKPKVKPKLERPKLYKVMLLNDDYTCSWFVTVVLKAVFRMS
EDTGRRVMMTAHRFGSAVVVVCERDIAETKAKEATDLGKEAGFPLMFTT
EPEE;

a third amino acid sequence comprising
                                     (Sequence ID No. 3)
SDSPVDLKPKPKVKPKLERPKLYKVMLLNDDYTPMSFVTVVLKAVFRMS
EDTGRRVMMTAHRFGSAVVVVCERDIAETKAKEATDLGKEAGFPLMFTT
EPEE;

A fourth amino acid sequence comprising
                                     (Sequence ID No. 4)
SDSPVDLKPKPKVKPKLERPKLYKVMLLNDDYTSGRFVTVVLKAVFRMS
EDTGRRVMMTAHRFGSAVVVVCERDIAETKAKEATDLGKEAGFPLMFTT
EPEE;

a fifth amino acid sequence comprising
                                     (Sequence ID No. 5)
SDSPVDLKPKPKVKPKLERPKLYKVMLLNDDYTPMPFVTVVLKAVFRMS
EDTGRRVMMTAHRFGSAVVVVCERDIAETKAKEATDLGKEAGFPLMFTT
EPEE;

a sixth amino acid sequence comprising
                                     (Sequence ID No. 6)
SDSPVDLKPKPKVKPKLERPKLYKVMLLNDDYTPREFVTVVLKAVFRMS
EDTGRRVMMTAHRFGSAVVVVSERDIAETKAKEATDLGKEAGFPLMFTT
EPEE;
``` a seventh amino acid sequence comprising
(Sequence ID No. 7)
SDSPVDLKPKPKVKPKLERPKLYKVMLLNDDYTPREFVTEVLKAVFNMS
EDQGRRVMMTAHRFGSAVVGVCTRDIAETKAKQATDLAREAGFPLMFTT
EPEE;

an eighth amino acid sequence comprising
(Sequence ID No. 8)
SDSPVDLKPKPKVKPKLERPKLYKVMLLNDDYTPMSFVTEVLKAVFNMS
EDQGRRVMMTAHRFGSAVVGVSTRDIAETKAKQATDLAREAGFPLMFTT
EPEE;

a ninth amino acid sequence comprising
(Sequence ID No. 9)
PSLYRVLILNDDYTPMEFVVYVLERFFNKSREDATRIMLHVHQNGVGVC
GVYTYEVAETKVAQVIDSARRHQHPLQCTMEKD;

a tenth amino acid sequence comprising; or
(Sequence ID No. 10)
NLEKIKKLRNVIKEIKKDNIKEADEHEKKEREKETSAWKVILYNDDIHK
FSYVTDVIVKVVGQISKAKAHTITVEAHSTGQALILSTWKSKAEKYCQE
LQQNGLTVSIIHESQLKDKQKK.

Disclosed is a binder complex for selectively identifying an amino acid, the binder complex comprising: an amino acid-specific binder; and an adjunct attached to the amino acid-specific binder, wherein the amino acid-specific binder binds selectively to a binding amino acid, and the amino acid-specific binder comprises:

a first amino acid sequence comprising
(Sequence ID No. 1)
SDSPVDLKPKPKVKPKLERPKLYKVMLLNDDYTCPSFVTVVLKAVFRMS
EDTGRRVMMTAHRFGSAVVVVCERDIAETKAKEATDLGKEAGFPLMFTT
EPEE;

a second amino acid sequence comprising
(Sequence ID No. 2)
SDSPVDLKPKPKVKPKLERPKLYKVMLLNDDYTCSWFVTVVLKAVFRMS
EDTGRRVMMTAHRFGSAVVVVCERDIAETKAKEATDLGKEAGFPLMFTT
EPEE;

a third amino acid sequence comprising
(Sequence ID No. 3)
SDSPVDLKPKPKVKPKLERPKLYKVMLLNDDYTPMSFVTVVLKAVFRMS
EDTGRRVMMTAHRFGSAVVVVCERDIAETKAKEATDLGKEAGFPLMFTT
EPEE;

A fourth amino acid sequence comprising
(Sequence ID No. 4)
SDSPVDLKPKPKVKPKLERPKLYKVMLLNDDYTSGRFVTVVLKAVFRMS
EDTGRRVMMTAHRFGSAVVVVCERDIAETKAKEATDLGKEAGFPLMFTT
EPEE;

a fifth amino acid sequence comprising
(Sequence ID No. 5)
SDSPVDLKPKPKVKPKLERPKLYKVMLLNDDYTPMPFVTVVLKAVFRMS
EDTGRRVMMTAHRFGSAVVVVCERDIAETKAKEATDLGKEAGFPLMFTT
EPEE;

a sixth amino acid sequence comprising
(Sequence ID No. 6)
SDSPVDLKPKPKVKPKLERPKLYKVMLLNDDYTPREFVTVVLKAVFRMS
EDTGRRVMMTAHRFGSAVVVVSERDIAETKAKEATDLGKEAGFPLMFTT
EPEE;

a seventh amino acid sequence comprising
(Sequence ID No. 7)
SDSPVDLKPKPKVKPKLERPKLYKVMLLNDDYTPREFVTEVLKAVFNMS
EDQGRRVMMTAHRFGSAVVGVCTRDIAETKAKQATDLAREAGFPLMFTT
EPEE;

an eighth amino acid sequence comprising
(Sequence ID No. 8)
SDSPVDLKPKPKVKPKLERPKLYKVMLLNDDYTPMSFVTEVLKAVFNMS
EDQGRRVMMTAHRFGSAVVGVSTRDIAETKAKQATDLAREAGFPLMFTT
EPEE;

a ninth amino acid sequence comprising
(Sequence ID No. 9)
PSLYRVLILNDDYTPMEFVVYVLERFFNKSREDATRIMLHVHQNGVGVC
GVYTYEVAETKVAQVIDSARRHQHPLQCTMEKD;

a tenth amino acid sequence comprising;
(Sequence ID No. 10)
NLEKIKKLRNVIKEIKKDNIKEADEHEKKEREKETSAWKVILYNDDIHK
FSYVTDVIVKVVGQISKAKAHTITVEAHSTGQALILSTWKSKAEKYCQE
LQQNGLTVSIIHESQLKDKQKK.

or an eleventh amino acid sequence with a homology of at least 30% compared to an amino acid sequence comprising the first amino acid sequence, the second amino acid sequence, the third amino acid sequence, the fourth amino acid sequence, the fifth amino acid sequence, the sixth amino acid sequence, the seventh amino acid sequence, the eighth amino acid sequence, the ninth amino acid sequence, or the tenth amino acid sequence.

Disclosed is a process for selectively identifying an N-terminal amino acid, the process comprising: providing an analyte; contacting a C-terminal end of the analyte with an anchor; anchoring the C-terminal end to the anchor to form an anchored analyte; contacting an N-terminal amino acid of the anchored analyte with a binder complex, the binder complex comprising: an amino acid-specific binder; and a taggant attached to the amino acid-specific binder; selectively binding the amino acid-specific binder of the binder complex to the N-terminal amino acid of the anchored analyte when the N-terminal amino acid is a binding amino acid to form a tagged complex; subjecting the taggant of the tagged complex to a stimulus; producing, by the taggant of the tagged complex, a taggant signal in response to the stimulus; detecting the taggant signal; and identifying the N-terminal amino acid based on the taggant signal, wherein the amino acid-specific binder binds selectively to the binding amino acid, and the amino acid-specific binder comprises:

a first amino acid sequence comprising
(Sequence ID No. 1)
SDSPVDLKPKPKVKPKLERPKLYKVMLLNDDYTCPSFVTVVLKAVFRMS
EDTGRRVMMTAHRFGSAVVVVCERDIAETKAKEATDLGKEAGFPLMFTT
EPEE;

a second amino acid sequence comprising
(Sequence ID No. 2)
SDSPVDLKPKPKVKPKLERPKLYKVMLLNDDYTCSWFVTVVLKAVFRMS
EDTGRRVMMTAHRFGSAVVVVCERDIAETKAKEATDLGKEAGFPLMFTT
EPEE;

a third amino acid sequence comprising
(Sequence ID No. 3)
SDSPVDLKPKPKVKPKLERPKLYKVMLLNDDYTPMSFVTVVLKAVFRMS
EDTGRRVMMTAHRFGSAVVVVCERDIAETKAKEATDLGKEAGFPLMFTT
EPEE;

A fourth amino acid sequence comprising
(Sequence ID No. 4)
SDSPVDLKPKPKVKPKLERPKLYKVMLLNDDYTSGRFVTVVLKAVFRMS
EDTGRRVMMTAHRFGSAVVVVCERDIAETKAKEATDLGKEAGFPLMFTT
EPEE;

a fifth amino acid sequence comprising
(Sequence ID No. 5)
SDSPVDLKPKPKVKPKLERPKLYKVMLLNDDYTPMPFVTVVLKAVFRMS
EDTGRRVMMTAHRFGSAVVVVCERDIAETKAKEATDLGKEAGFPLMFTT
EPEE;

a sixth amino acid sequence comprising
(Sequence ID No. 6)
SDSPVDLKPKPKVKPKLERPKLYKVMLLNDDYTPREFVTVVLKAVFRMS
EDTGRRVMMTAHRFGSAVVVVSERDIAETKAKEATDLGKEAGFPLMFTT
EPEE;

a seventh amino acid sequence comprising
(Sequence ID No. 7)
SDSPVDLKPKPKVKPKLERPKLYKVMLLNDDYTPREFVTEVLKAVFNMS
EDQGRRVMMTAHRFGSAVVGVCTRDIAETKAKQATDLAREAGFPLMFTT
EPEE;

an eighth amino acid sequence comprising
(Sequence ID No. 8)
SDSPVDLKPKPKVKPKLERPKLYKVMLLNDDYTPMSFVTEVLKAVFNMS
EDQGRRVMMTAHRFGSAVVGVSTRDIAETKAKQATDLAREAGFPLMFTT
EPEE;

a ninth amino acid sequence comprising
(Sequence ID No. 9)
PSLYRVLILNDDYTPMEFVVYVLERFFNKSREDATRIMLHVHQNGVGVC
GVYTYEVAETKVAQVIDSARRHQHPLQCTMEKD;

a tenth amino acid sequence comprising; or
(Sequence ID No. 10)
NLEKIKKLRNVIKEIKKDNIKEADEHEKKEREKETSAWKVILYNDDIHK
FSYVTDVIVKVVGQISKAKAHTITVEAHSTGQALILSTWKSKAEKYCQE
LQQNGLTVSIIHESQLKDKQKK.

or an eleventh amino acid sequence with a homology of at least 30% compared to an amino acid sequence comprising the first amino acid sequence, the second amino acid sequence, the third amino acid sequence, the fourth amino acid sequence, the fifth amino acid sequence, the sixth amino acid sequence, the seventh amino acid sequence, the eighth amino acid sequence, the ninth amino acid sequence, or the tenth amino acid sequence.

Disclosed is a process for selectively isolating an analyte, the process comprising: contacting an amino acid-specific binder with an analyte comprising a protein, a peptide, an amino acid, or a combination comprising at least one of foregoing; selectively binding the amino acid-specific binder to the N-terminal amino acid of the analyte when the N-terminal amino acid is a binding amino acid to form an isolation complex; separating the isolation complex from a fluid in which the isolation complex is disposed to selectively isolating the analyte, wherein the amino acid-specific binder binds selectively to the binding amino acid, and the amino acid-specific binder comprises:

a first amino acid sequence comprising
(Sequence ID No. 1)
SDSPVDLKPKPKVKPKLERPKLYKVMLLNDDYTCPSFVTVVLKAVFRMS
EDTGRRVMMTAHRFGSAVVVVCERDIAETKAKEATDLGKEAGFPLMFTT
EPEE;

a second amino acid sequence comprising
(Sequence ID No. 2)
SDSPVDLKPKPKVKPKLERPKLYKVMLLNDDYTCSWFVTVVLKAVFRMS
EDTGRRVMMTAHRFGSAVVVVCERDIAETKAKEATDLGKEAGFPLMFTT
EPEE;

a third amino acid sequence comprising
(Sequence ID No. 3)
SDSPVDLKPKPKVKPKLERPKLYKVMLLNDDYTPMSFVTVVLKAVFRMS
EDTGRRVMMTAHRFGSAVVVVCERDIAETKAKEATDLGKEAGFPLMFTT
EPEE;

A fourth amino acid sequence comprising
(Sequence ID No. 4)
SDSPVDLKPKPKVKPKLERPKLYKVMLLNDDYTSGRFVTVVLKAVFRMS
EDTGRRVMMTAHRFGSAVVVVCERDIAETKAKEATDLGKEAGFPLMFTT
EPEE;

a fifth amino acid sequence comprising
(Sequence ID No. 5)
SDSPVDLKPKPKVKPKLERPKLYKVMLLNDDYTPMPFVTVVLKAVFRMS
EDTGRRVMMTAHRFGSAVVVVCERDIAETKAKEATDLGKEAGFPLMFTT
EPEE;

a sixth amino acid sequence comprising
(Sequence ID No. 6)
SDSPVDLKPKPKVKPKLERPKLYKVMLLNDDYTPREFVTVVLKAVFRMS
EDTGRRVMMTAHRFGSAVVVVSERDIAETKAKEATDLGKEAGFPLMFTT
EPEE;

a seventh amino acid sequence comprising
(Sequence ID No. 7)
SDSPVDLKPKPKVKPKLERPKLYKVMLLNDDYTPREFVTEVLKAVFNMS
EDQGRRVMMTAHRFGSAVVGVCTRDIAETKAKQATDLAREAGFPLMFTT
EPEE;

an eighth amino acid sequence comprising
(Sequence ID No. 8)
SDSPVDLKPKPKVKPKLERPKLYKVMLLNDDYTPMSFVTEVLKAVFNMS
EDQGRRVMMTAHRFGSAVVGVSTRDIAETKAKQATDLAREAGFPLMFTT
EPEE;

a ninth amino acid sequence comprising
(Sequence ID No. 9)
PSLYRVLILNDDYTPMEFVVYVLERFFNKSREDATRIMLHVHQNGVGVC
GVYTYEVAETKVAQVIDSARRHQHPLQCTMEKD;

a tenth amino acid sequence comprising;
(Sequence ID No. 10)
NLEKIKKLRNVIKEIKKDNIKEADEHEKKEREKETSAWKVILYNDDIHK
FSYVTDVIVKVVGQISKAKAHTITVEAHSTGQALILSTWKSKAEKYCQE
LQQNGLTVSIIHESQLKDKQKK.

or an eleventh amino acid sequence with a homology of at least 30% compared to an amino acid sequence comprising the first amino acid sequence, the second amino acid sequence, the third amino acid sequence, the fourth amino acid sequence, the fifth amino acid sequence, the sixth amino acid sequence, the seventh amino acid sequence, the eighth amino acid sequence, the ninth amino acid sequence, or the tenth amino acid sequence.

BRIEF DESCRIPTION OF THE DRAWINGS

The following description should not be considered limiting in any way. With reference to the accompanying drawings, like elements are numbered alike.

FIG. 19 shows alignment of *Agrobacterium tumefaciens* ClpS2 (Sequence ID No. 11) and *Plasmodium falciparum* ClpS (Sequence ID. No. 12) protein sequences (21.43% identity). Identical positions are highlighted in darkest. Black triangles indicate proposed substrate contacts based on the crystal structure of *A. tumefaciens* ClpS2 bound to L-phenylalaninamide. Residues highlighted in yellow were mutated in constructs selected from initial error-prone libraries for increased Phe binding. A box around residues 34P, 35R, and 36E of the *A. tumefaciens* ClpS2 highlights residues that were mutated to all 20 amino acids in the second library;

DETAILED DESCRIPTION

Figure 1:
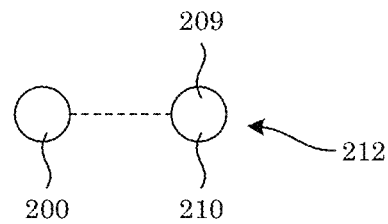
FIG. 1 shows an amino acid-specific binder selectively bound to an amino acid that is a binding amino acid of an analyte in panel A, and panel B shows a non-binding amino acid unbound to an amino acid-specific binder.
Figure 1:
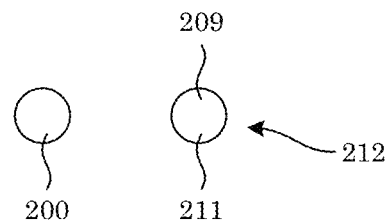

A detailed description of one or more embodiments is presented herein by way of exemplification and not limitation.

It has been discovered that an amino acid-specific binder herein selectively binds to a binding amino acid selected from a group of specific amino acids. Indeed, the amino acid-specific binder overcomes a central challenge in single-molecule protein sequencing technology and provides high-fidelity, sequential recognition, detection of specific amino acids that can be included in a peptide sequence. Moreover, the amino acid-specific binder overcomes lack of selectivity involved with an N-End Rule Pathway adaptor protein (NERPap), ClpS, that natively recognizes an N-terminal amino acid (NAA) on a peptide chain wherein the NERPap lacks selectivity and affinity for peptide sequencing. Beneficially and unexpectedly, the amino acid-specific binder provides selectivity by including novel sequence variants of *A. tumefaciens* ClpS2, a ClpS protein, such that the amino acid-specific binder has enhanced affinity and selectivity for various amino acids including phenylalanine (Phe), tryptophan (Trp), and tyrosine (Tyr), which can occur as a single binding amino acid or at an N-terminus of a peptide or protein. Advantageously, the amino acid-specific binder determines a sequence or fingerprint of amino acids in a peptide or protein when used iteratively.

Amino acid-specific binder 200 selectively binds to binding amino acid 210 in analyte 212. In an embodiment, amino acid-specific binder 200 is a first amino acid sequence including X1-C-P-S-X2-V-X3-R-X4-T-X5-C-E-X6-E-X7-G-K-X8; a second amino acid sequence including X1-C-S-W-X2-V-X3-R-X4-T-X5-C-E-X6-E-X7-G-K-X8; a third amino acid sequence including X1-P-M-S-X2-V-X3-R-X4-T-X5-C-E-X6-E-X7-G-K-X8; a fourth amino acid sequence including X1-S-G-R-X2-V-X3-R-X4-T-X5-C-E-X6-E-X7-G-K-X8; a fifth amino acid sequence including X1-P-M-P-X2-V-X3-R-X4-T-X5-C-E-X6-E-X7-G-K-X8; a sixth amino acid sequence including X1-P-R-E-X2-V-X3-R-X4-T-X5-S-E-X6-E-X7-G-K-X8; a seventh amino acid sequence including X1-P-R-E-X2-E-X3-N-X4-Q-X5-C-T-X6-Q-X7-A-R-X8; or an eighth amino acid sequence including X1-P-M-S-X2-E-X3-N-X4-Q-X5-S-T-X6-Q-X7-A-R-X8; wherein: X1 includes an amino acid sequence including SDSPVDLKPKPKVKPKLERPK- LYKVMLLNDDYT (Sequence ID No. 20); X2 includes an amino acid sequence including FVT; X3 includes an amino acid sequence including VLKAVF (Sequence ID No. 21); X4 includes an amino acid sequence including MSED (Sequence ID No. 22); X5 includes an amino acid sequence including GRRVMMTAHRFGSAVVVV (Sequence ID No. 23); X6 includes an amino acid sequence including RDIAETKAK (Sequence ID No. 24); X7 includes an amino acid sequence including ATDL (Sequence ID No. 25); and X8 includes an amino acid sequence including EAGFPLMFTTEPEE (Sequence ID No. 26), such that a total percentage amount of substitutions and deletions to X1, X2, X3, X4, X5, X6, X7, and X8 is from 0% to less than 30%, exclusive of SDSPVDLKPKPKVKPKLERPKLYKVMLLNDDYTPMEFVTVVLKAVFRMSEDTGRRVMMTAHRFGSAWWCERDIAETKAKEATDLGKEAGFPLMFTTEPEE (Sequence ID No. 27).

In an embodiment, amino acid-specific binder 200 is a protein that includes an amino acid sequence that is (Sequence ID No. 1)
SDSPVDLKPKPKVKPKLERPKLYKVMLLNDDYTCPSFVTVVLKAVFRMS
EDTGRRVMMTAHRFGSAVVVVCERDIAETKAKEATDLGKEAGFPLMFTT
EPEE;

(Sequence ID No. 2)
SDSPVDLKPKPKVKPKLERPKLYKVMLLNDDYTCSWFVTVVLKAVFRMS
EDTGRRVMMTAHRFGSAVVVVCERDIAETKAKEATDLGKEAGFPLMFTT
EPEE;

(Sequence ID No. 3)
SDSPVDLKPKPKVKPKLERPKLYKVMLLNDDYTPMSFVTVVLKAVFRMS
EDTGRRVMMTAHRFGSAVVVVCERDIAETKAKEATDLGKEAGFPLMFTT
EPEE;

(Sequence ID No. 4)
SDSPVDLKPKPKVKPKLERPKLYKVMLLNDDYTSGRFVTVVLKAVFRMS
EDTGRRVMMTAHRFGSAVVVVCERDIAETKAKEATDLGKEAGFPLMFTT
EPEE;

(Sequence ID No. 5)
SDSPVDLKPKPKVKPKLERPKLYKVMLLNDDYTPMPFVTVVLKAVFRMS
EDTGRRVMMTAHRFGSAVVVVCERDIAETKAKEATDLGKEAGFPLMFTT
EPEE;

(Sequence ID No. 6)
SDSPVDLKPKPKVKPKLERPKLYKVMLLNDDYTPREFVTVVLKAVFRMS
EDTGRRVMMTAHRFGSAVVVVSERDIAETKAKEATDLGKEAGFPLMFTT
EPEE;

(Sequence ID No. 7)
SDSPVDLKPKPKVKPKLERPKLYKVMLLNDDYTPREFVTEVLKAVFNMS
EDQGRRVMMTAHRFGSAVVGVCTRDIAETKAKQATDLAREAGFPLMFTT
EPEE;

(Sequence ID No. 8)
SDSPVDLKPKPKVKPKLERPKLYKVMLLNDDYTPMSFVTEVLKAVFNMS
EDQGRRVMMTAHRFGSAVVGVSTRDIAETKAKQATDLAREAGFPLMFTT
EPEE;

(Sequence ID No. 9)
PSLYRVLILNDDYTPMEFVVYVLERFFNKSREDATRIMLHVHQNGVGVC
GVYTYEVAETKVAQVIDSARRHQHPLQCTMEKD;

(Sequence ID No. 10)
NLEKIKKLRNVIKEIKKDNIKEADEHEKKEREKETSAWKVILYNDDIHK
FSYVTDVIVKVVGQISKAKAHTITVEAHSTGQALILSTWKSKAEKYCQE
LQQNGLTVSIIHESQLKDKQKK;

or an amino acid sequence with a homology of at least 30% compared to an amino acid sequence comprising the amino acid sequence with Sequence ID No. 1, Sequence ID No. 2, Sequence ID No. 3, Sequence ID No. 4, Sequence ID No. 5, Sequence ID No. 6, Sequence ID No. 7, Sequence ID No. 8, Sequence ID No. 9, or Sequence ID No. 10. Amino acid-specific binder 200 binds selectively to binding amino acid 210 selected from the group consisting of isoleucine, leucine, phenylalanine, tryptophan, tyrosine, and valine; and chemically modified amino acids phenylalanine, tryptophan, tyrosine, isoleucine, leucine, and valine. Accordingly, with reference to FIG. 1, amino acid-specific binder 200 selectively binds to binding amino acid 210 of analyte 212 but does not bind to non-binding amino acid 211.

In an embodiment, the amino acid sequence includes:

(Sequence ID No. 1)
SDSPVDLKPKPKVKPKLERPKLYKVMLLNDDYTCPSFVTVVLKAVFRMS
EDTGRRVMMTAHRFGSAVVVVCERDIAETKAKEATDLGKEAGFPLMFTT
EPEE;

(Sequence ID No. 2)
SDSPVDLKPKPKVKPKLERPKLYKVMLLNDDYTCSWFVTVVLKAVFRMS
EDTGRRVMMTAHRFGSAVVVVCERDIAETKAKEATDLGKEAGFPLMFTT
EPEE;

(Sequence ID No. 3)
SDSPVDLKPKPKVKPKLERPKLYKVMLLNDDYTPMSFVTVVLKAVFRMS
EDTGRRVMMTAHRFGSAVVVVCERDIAETKAKEATDLGKEAGFPLMFTT
EPEE;

(Sequence ID No. 4)
SDSPVDLKPKPKVKPKLERPKLYKVMLLNDDYTSGRFVTVVLKAVFRMS
EDTGRRVMMTAHRFGSAVVVVCERDIAETKAKEATDLGKEAGFPLMFTT
EPEE;

(Sequence ID No. 5)
SDSPVDLKPKPKVKPKLERPKLYKVMLLNDDYTPMPFVTVVLKAVFRMS
EDTGRRVMMTAHRFGSAVVVVCERDIAETKAKEATDLGKEAGFPLMFTT
EPEE;

(Sequence ID No. 6)
SDSPVDLKPKPKVKPKLERPKLYKVMLLNDDYTPREFVTVVLKAVFRMS
EDTGRRVMMTAHRFGSAVVVVSERDIAETKAKEATDLGKEAGFPLMFTT
EPEE;

(Sequence ID No. 7)
SDSPVDLKPKPKVKPKLERPKLYKVMLLNDDYTPREFVTEVLKAVFNMS
EDQGRRVMMTAHRFGSAVVGVCTRDIAETKAKQATDLAREAGFPLMFTT
EPEE;

(Sequence ID No. 8)
SDSPVDLKPKPKVKPKLERPKLYKVMLLNDDYTPMSFVTEVLKAVFNMS
EDQGRRVMMTAHRFGSAVVGVSTRDIAETKAKQATDLAREAGFPLMFTT
EPEE;

(Sequence ID No. 9)
PSLYRVLILNDDYTPMEFVVYVLERFFNKSREDATRIMLHVHQNGVGVC
GVYTYEVAETKVAQVIDSARRHQHPLQCTMEKD;

(Sequence ID No. 10)
NLEKIKKLRNVIKEIKKDNIKEADEHEKKEREKETSAWKVILYNDDIHK
FSYVTDVIVKVVGQISKAKAHTITVEAHSTGQALILSTWKSKAEKYCQE
LQQNGLTVSIIHESQLKDKQKK;

According to an embodiment, amino acid-specific binder 200 is a protein with Sequence ID No. 1 and binds selectively to phenylalanine, tryptophan, or leucine.

According to an embodiment, amino acid-specific binder 200 is a protein with Sequence ID No. 2 and binds selectively to phenylalanine, tyrosine, or isoleucine.

According to an embodiment, amino acid-specific binder 200 is a protein with Sequence ID No. 3 and binds selectively to phenylalanine, tryptophan, chemically modified phenylalanine, and chemically modified tryptophan.

According to an embodiment, amino acid-specific binder 200 is a protein with Sequence ID No. 4 and binds selectively to phenylalanine, tryptophan, tyrosine, chemically modified phenylalanine, chemically modified tryptophan, and chemically modified tyrosine.

According to an embodiment, amino acid-specific binder 200 is a protein with Sequence ID No. 5 and binds selectively to phenylalanine, tryptophan, tyrosine, isoleucine, leucine, valine, or chemically modified amino acids phenylalanine, tryptophan, tyrosine, isoleucine, leucine, and valine.

According to an embodiment, amino acid-specific binder 200 is a protein with Sequence ID No. 6 and binds selectively to phenylalanine, tryptophan, tyrosine, isoleucine, leucine, valine, or chemically modified amino acids phenylalanine, tryptophan, tyrosine, isoleucine, leucine, and valine.

According to an embodiment, amino acid-specific binder 200 is a protein with Sequence ID No. 7 and binds selectively to phenylalanine, tryptophan, tyrosine, isoleucine, leucine, valine, or chemically modified amino acids phenylalanine, tryptophan, tyrosine, isoleucine, leucine, and valine.

According to an embodiment, amino acid-specific binder 200 is a protein with Sequence ID No. 8 and binds selectively to phenylalanine, tryptophan, or chemically modified phenylalanine or chemically modified tryptophan.

According to an embodiment, amino acid-specific binder 200 is a protein with Sequence ID No. 9 and binds selectively to tyrosine, isoleucine, leucine, or valine.

According to an embodiment, amino acid-specific binder 200 is a protein with Sequence ID No. 10 and binds selectively to phenylalanine, tryptophan, tyrosine, isoleucine, leucine, valine, or chemically modified amino acids phenylalanine, tryptophan, tyrosine, isoleucine, leucine, and valine.

According to an embodiment, amino acid-specific binder 200 is a protein with a sequence homology of at least 30% compared to an amino acid sequence selected from the group consisting essentially of the amino acid sequence with Sequence ID No. 1, Sequence ID No. 2, Sequence ID No. 3, Sequence ID No. 4, Sequence ID No. 5, Sequence ID No. 6, Sequence ID No. 7, Sequence ID No. 8, Sequence ID No. 9, and Sequence ID No. 10 and binds selectively to isoleucine, leucine, phenylalanine, tryptophan, tyrosine, valine or chemically modified amino acids phenylalanine, tryptophan, tyrosine, isoleucine, leucine, and valine.

Figure 2:
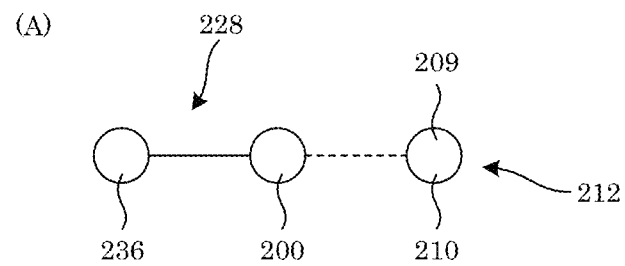
FIG. 2 shows an amino acid-specific binder of a binder complex selectively bound to a binding amino acid of an analyte in panel A, and panel B shows a non-binding amino acid unbound to an amino acid-specific binder of a binder complex.
Figure 2:
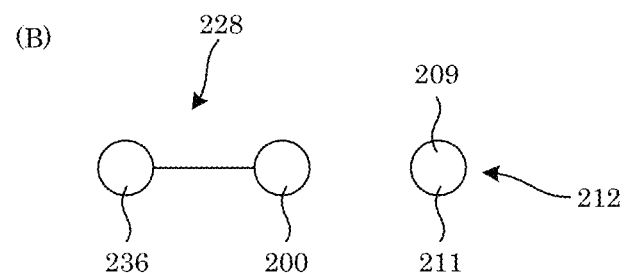
Figure 3:
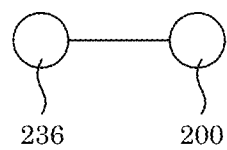
FIG. 3 shows a binder complex in an absence of an intervening member in panel A and inclusion of an intervening member in panel B.
Figure 3:
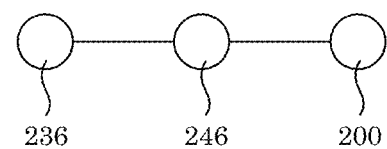

Binder complex 228 selectively identifies an amino acid. In an embodiment, binder complex 228 includes amino acid-specific binder 200 and adjunct 236 attached to amino acid-specific binder 200. Attachment of adjunct 236 to amino acid-specific binder 200 can include a covalent bond, an ionic bond, electrostatic interaction (e.g., a π-cation interaction, dipole-dipole interaction, a multi-pole interaction, and the like), intercalation, a clathrate arrangement (e.g., with adjunct 236 partially or wholly trapped in amino acid-specific binder 200 or vice-versa, such that amino acid-specific binder 200 can still selectively bind to binding amino acid 210, e.g., of analyte 212), and the like. Further, adjunct 236 can be attached to amino acid-specific binder 200 either directly, indirectly, or a combination thereof. With reference to FIG. 3, when adjunct 236 is directly attached to amino acid-specific binder 200, direct attachment occurs in an absence of an intervening member between adjunct 236 and amino acid-specific binder 200 as shown in panel A. When adjunct 236 is indirectly attached to amino acid-specific binder 200 as shown in panel B, indirect attachment occurs in a presence of the intervening member 246 between adjunct 236 and amino acid-specific binder 200. Accordingly, with reference to FIG. 2, amino acid-specific binder 200 selectively binds to binding amino acid 210 of analyte 212 but does not bind to non-binding amino acid 211.

Figure 4:
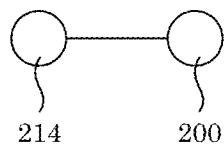
FIG. 4 shows a binder complex that includes an amino acid-specific binder attached to a taggant in panel A, a protein in panel B, a chemical modifier in panel C, and a substrate in panel D.
Figure 4:
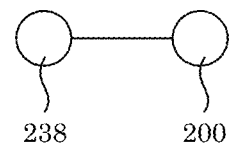
Figure 4:
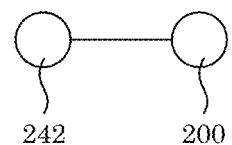
Figure 4:
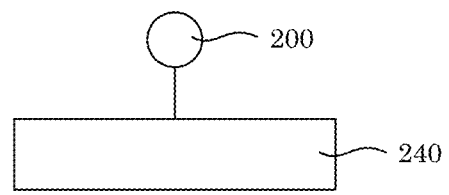
Figure 5:
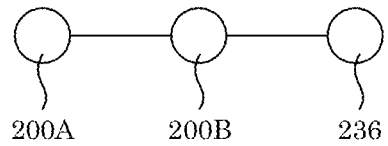
FIG. 5 shows a binder complex that includes a plurality of amino acid-specific binders attached to an adjunct in panel A and panel B and attached to a plurality of adjuncts in panel C.
Figure 5:
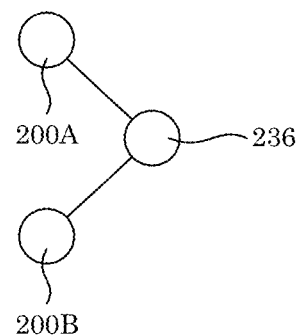
Figure 5:
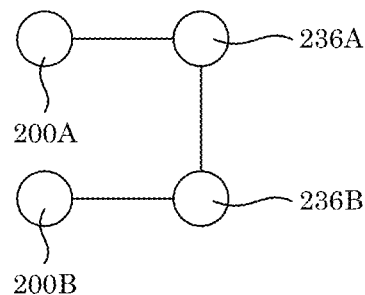

In binder complex 228, with reference to FIG. 3, adjunct 236 can determine a position or identity of amino acid-specific binder 200 and determine if amino acid-specific binder 200 is bound to analyte 212. Adjunct 236 can be taggant 214, protein 238, substrate 240, chemical modifier 242, or a combination thereof, e.g., as shown in FIG. 4. In an embodiment, adjunct 236 includes taggant 214. In an embodiment, adjunct 236 includes a substrate such that analyte 212 can be immobilized when in contact with amino acid-specific binder 200. Binder complex 228 can include an arbitrary number of amino acid-specific binder 200 and adjunct 236 that can be connectedly attached in an arbitrary arrangement as shown in FIG. 5.

Protein 238 can include a protein to facilitate expression or purification of amino-acid specific binder 200 such as a protein with a functional group that can be immobilized on a resin, an antibody, Protein A, Protein G, a peptide of six histidine residues, Glutathione S-transferase, maltose binding protein, biotin, or streptavidin. Moreover, protein 238 can include a protein with a reactive property such as enzymatic activity, a protease cleavage site, or fluorescence that can be stimulated to produce a signal and can be green fluorescent protein, horseradish peroxidase, luciferase, and the like. Moreover, protein 238 can include proteins with a selected molecular weight, isoelectric point, or functional group that can facilitate separation of binding complex 238, e.g., by dialysis, chromatography, or gradient centrifugation. Exemplary proteins 238 include an immunoglobulin, a high molecular weight protein (HMWP), DNA-binding protein, oligosaccharide binding protein, and the like. In an embodiment, protein 238 is biotinylated and can be attached to a substrate through interaction with streptavidin.

Substrate 240 can include magnetic beads, fluorescent beads, silica coverslips, or microplates to attach amino acid-specific binder 200 to the substrate surface and can be a functionalized glass slide. Moreover, the substrate can be used for localization of amino acid-specific binder 200 by providing separation either by size or magnetism or physical movement of the substrate. The substrate can also be used to detect a taggant signal such as with fluorescent microscopy and can be a functionalized surface that is optically clear. Exemplary substrates 240 include NHS-ester functionalized glass slides, streptavidin coated magnetic beads or microplates, a nickel coated resin, and the like. In an embodiment, substrate 240 includes a nickel coated resin.

Chemical modifier 242 can include a reactive species that can be used in a non-covalent binding reaction or a cross-linking reaction or can be used to amplify a signal. Exemplary chemical modifiers 242 include click-chemistry compatible moieties, N-hydroxysuccinimide esters, biotin, maleimide, hydrazide, carbodiimide compounds for carboxylic acid cross-linking, photocatalysts, or electrocatalysts. In an embodiment, chemical modifier 242 includes an azide.

Exemplary taggant 214 are listed in Table 1 and can include a fluorescent moiety that can include embedded a fluorophore disposed in a shell, an electrochemical moiety, chemiluminescent moiety, Forster resonance energy transfer (FRET) pair, catalytic enzyme, chemical modification, or a combination comprising at least one of the foregoing moieties, that transduce or amplify stimulus 218 to a measurable response as taggant signal 216 for detecting a presence of amino acid-specific binder 200. In an embodiment, taggant 214 is a fluorophore (e.g. a fluorophore commercially available as ALEXAFLUOR such as ALEXAFLUOR647 and the like) that includes conjugated electrons to produce fluorescence upon stimulation by stimulant 218. Exemplary taggants 214 include horseradish peroxidase, fluorescein, rhodamine, and the like. In an embodiment, taggant 214 includes a fluorescently labelled dye (e.g., a dye such as commercially available as ATT0532). Taggant 214 produces taggant signal 216 in response to being subjected to stimulus 218.

TABLE 1

| Taggant | Complex formation method | Stimulant | Signal | Detection |
|---|---|---|---|---|
| Fluorophore | NHS-ester lysine sidechain | Photon | Photon | intensity or wavelength |
| Chemiluminescence | Luciferase fusion | ATP | Photon | Intensity |
| Electrochemiluminescence | Fusion with Ru(Bpy)3 | Electrode potential | photon | PMT |
| FRET pair | a fluorophore on amino acid-specific binder 200, a fluorophore on analyte 212, or fluorophores on amino acid-specific binder 200 | Photon | Photon | Intensity or wavelength |
| Catalytic enzyme | Horseradish peroxidase fusion | Addition of chromogenic substrate | Absorbance at a wavelength | Spectrophotometer |
| Radioactive element | $^{35}$S-methionine, $^{32}$P-phosphorylation, or tritium labeling of amino acid binder 200 | None | Radioactivity | Scintillation counting or radio image |

Stimulus 218 can include light emitted from a lamp, laser, LED, or a chromogenic substrate such as tetramethyl benzidine (TMB). Exemplary stimulus 218 includes laser light such as 30 mW, 488 nm laser light. In an embodiment, stimulus 218 is a photon, e.g., from a light source such as a laser, flash lamp, and the like. In an embodiment, stimulus 218 is a redox potential pulse.

Taggant signal 216 can have a temporal duration suitable for detection by an electrical amplifier, photodetector, scintillator, camera, and the like. In an embodiment, taggant signal 216 is fluorescence emission that is detected, e.g., by a detector such as a microscope that transmits the fluorescence to a CCD camera, wherein the location of emission can be correlated with the intensity of the signal.

In binder complex 228, with regard to indirect attachment of adjunct 236 to amino acid-specific binder 200, intervening member 246 can include a linker to connect adjunct 236 to amino acid-specific binder 200 but that does not provide additional functionality other than linking the two together. Intervening member 246 can be a protein, peptide, chemical moiety, nucleic acid, and the like. Moreover, intervening member 246 can be chemically inert such that it does not interfere with binding or signaling. Exemplary intervening members 264 include a poly-glycine or serine peptide, a polyethylene glycol (PEG), a glycan, an oligonucleotide, and the like. In an embodiment, intervening member 264 includes a GSGG peptide.

Figure 6:
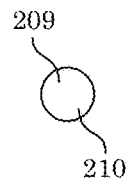
FIG. 6 shows an analyte that includes a binding amino acid in panel A, a non-binding amino acid in panel B, a binding amino acid and non-binding amino acid in panel C, and an analyte that is a peptide or protein that includes a plurality of amino acids in panel D and panel E.
Figure 6:
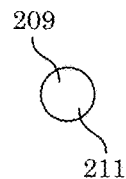
Figure 6:
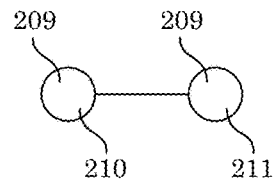
Figure 6:
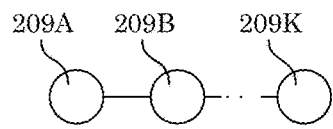
Figure 6:
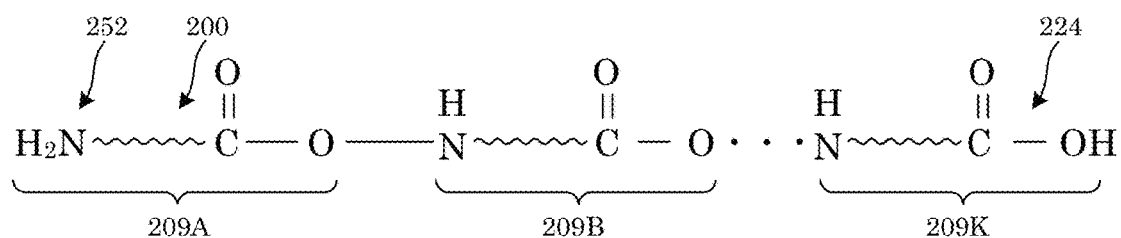

Amino acids 209 include binding amino acid 210 and analyte 212 as shown in FIG. 6. Here, in analyte 212, peptide 248 and protein 250 include a plurality of amino acids 209 (e.g., 209A, 209B, . . . , 209k) interconnected and terminating with N-terminal amino acid 220 that has free amine 252 and penultimate residue 234 and terminating with C-terminal end 224.

Amino acid-specific binder 200 selectively binds to binding amino acid 210 of analyte 212. Analyte 212 can include binding amino acid 210, non-binding amino acid 211, peptide 248, protein 250, or a combination thereof. Exemplary analytes 212 include proteins, peptides, free amino acids, and the like. In an embodiment, analyte 212 includes a protein that is cleaved using trypsin to produce a mixture of analytes 212 including binding amino acids 210 and non-binding amino acids 211.

Amino acid-specific binder 200 selectively binds to binding amino acid 210. Binding amino acid 210 can include certain naturally occurring amino acids, modified naturally occurring amino acids, non-naturally occurring amino acids, or modified non-naturally occurring amino acids. Selective binding of amino acid-specific binder 200 to binding amino acid 210 isolates binding amino acid 210 from other components in a fluid, identifies binding amino acid 210 as a particular species of amino acid (e.g., Phe, Trp, Tyr), and the like.

As used herein, "naturally occurring amino acid" refers to the 20 naturally occurring amino acids. Binding amino acids 210 that are naturally occurring amino acids are selected from group consisting of phenylalanine, tryptophan, tyrosine, leucine, isoleucine, and valine. As used herein, "modified naturally occurring amino acid" refers to naturally occurring amino acids in which a sidechain has been modified. Exemplary modifications include methylation, phosphorylation, glycosylation, deamination, oxidation, or selenocysteine formation. Accordingly, binding amino acids 210 that are modified naturally occurring amino acids include phosphotyrosine, N-acetylated valine, kynurenine and the like.

As used herein, "non-naturally occurring amino acid" refers to amino acids that are not naturally incorporated into peptide or protein polymers but can be synthetically incorporated into a polypeptide. Exemplary non-naturally occurring amino acids are D-amino acids, homo-amino acids, and amino acids with a non-natural sidechain such as biphenylalanine or azidophenylalanine. Accordingly, binding amino acids 210 that are non-naturally occurring amino acids include 5-bromo-tryptophan, homophenylalanine, homophenylalanine methyl ester hydrochloride, and the like.

As used herein, "modified non-naturally occurring amino acid" refers to a non-naturally occurring amino acid that has been modified. Exemplary modifications include such as methylation, phosphorylation, glycosylation, deamination, oxidation, or selenocysteine formation. Accordingly, binding amino acids 210 that are modified non-naturally occurring amino acids include 5-bromo-tryptophan, homophenylalanine, homopenylalanine methyl ester hydrochloride, and the like.

Amino acid-specific binder 200 does not bind to non-binding amino acid 211. Non-binding amino acid 211 can be a naturally occurring or non-naturally occurring amino acid exclusive of binding amino acid 210. Exemplary non-binding amino acids 211 include arginine, alanine, serine, threonine, proline, aspartic acid, asparagine, glutamine, glutamic acid. Since amino acid-specific binder 200 does not bind to non-binding amino acid 211 but does selectively bind to binding amino acid 210, non-binding amino acid 211 is determined as not belonging to the group of binding amino acids 210 selectively bound by amino acid-specific binder 200. Accordingly, while binding of amino acid-specific binder 200 to binding amino acid 210 can be used to isolate binding amino acid 210 from other components in a fluid, identify binding amino acid 210 as a particular species of amino acid (e.g., Phe, Trp, Tyr), and the like, not binding non-binding amino acid 211 can be used separate non-binding amino acid 211 from binding amino acid 210 and, by negative implication, determine a set of possible identities for binding amino acid 210.

Peptide 248 can include a plurality of amino acids, including binding amino acid 210, non-binding amino acid 211, or a combination thereof. Moreover, amino acids in peptide 248 are arranged to include N-terminal amino acid 220 and C-terminal end 224. Peptide 248 can be naturally occurring or can be a portion of a longer peptide or protein. Exemplary peptides 248 include a peptide from a proteolytic or tryptic digest of an isolated protein or protein found in blood or serum. Binding of amino acid-specific binder 200 to binding amino acid 210 can be used to isolate binding amino acid 210 from other components in a fluid, identify binding amino acid 210 as a particular species of amino acid (e.g., Phe, Trp, Tyr), and the like.

Protein 250 can include a plurality of amino acids, including binding amino acid 210, non-binding amino acid 211, or a combination thereof. Moreover, amino acids in protein 250 are arranged to include N-terminal amino acid 220 and C-terminal end 224. Protein 250 can be obtained from a mixture of proteins as found within a blood or serum sample. In an embodiment, protein 250 includes serum proteins.

Figure 7:
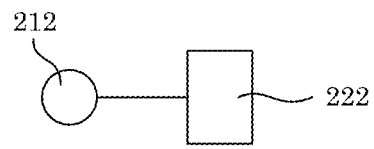
FIG. 7 shows an anchored analyte in an absence of an intervening member in panel A and inclusion of an intervening member in panel B.
Figure 7:
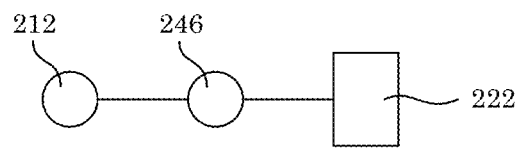

In some embodiments, with reference to FIG. 7, analyte 212 forms anchored analyte 226 in combination with anchor 222. Anchor 222 can include a substrate containing a surface on which to immobilize the analyte such that it can be sequestered or measured. Anchor 222 can be a resin, glass slide, magnetic bead. Exemplary anchor 222 includes a streptavidin coated sensor, microplate, and the like. In an embodiment, anchor 222 includes a streptavidin coated microplate, and intervening member 264 includes biotin.

Exemplary anchored analyte 226 includes a peptide analyte 212 anchored via the lysine sidechain to an NHS-ester coated glass slide and the like. It is contemplated that attachment of analyte 212 to anchor 222 can include a covalent bond, an ionic bond, electrostatic interaction (e.g., a π-cation interaction, dipole-dipole interaction, a multi-pole interaction, and the like), intercalation, a clathrate arrangement (e.g., with analyte 212 partially or wholly trapped in anchor 222 or vice-versa, such that N-terminal amino acid 220 or binding amino acid 210 is exposed to amino acid-specific binder 200 for selectively binding), and the like. Further, analyte 212 can be attached to anchor 222 either directly, indirectly, or a combination thereof. When analyte 212 is directly attached to anchor 222, direct attachment occurs in an absence of an intervening member between analyte 212 and anchor 222. When analyte 212 is indirectly attached to anchor 222, indirect attachment occurs in a presence of the intervening member 246 between analyte 212 and anchor 222.

In an embodiment, anchored analyte 226 includes a peptide analyte 212 anchored via the lysine sidechain to an NHS-ester coated glass slide and the like.

Figure 8:
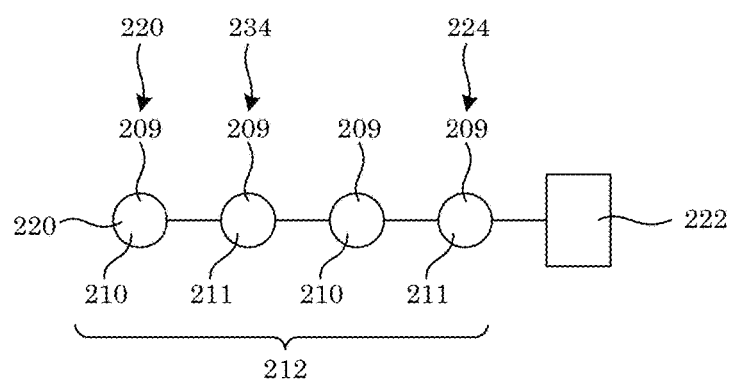
FIG. 8 shows an anchored analyte in panel A; and a tagged complex in panel B.
Figure 8:
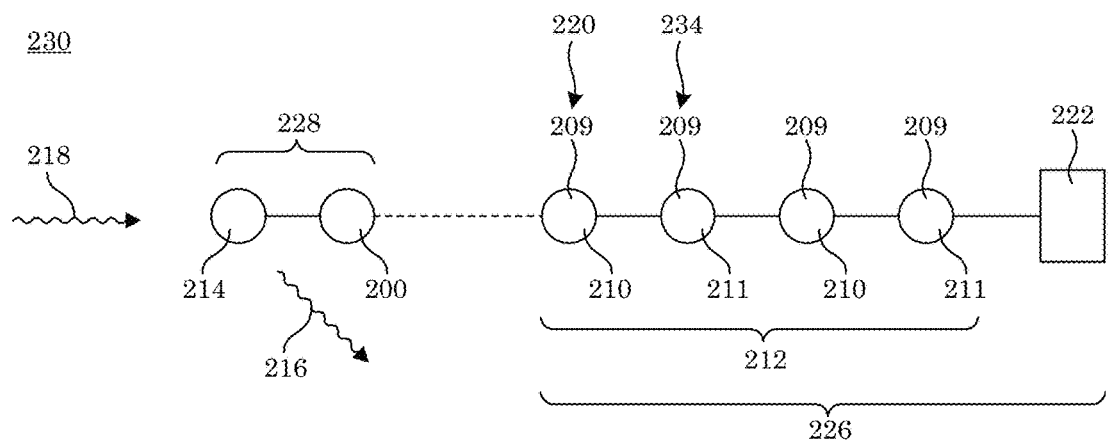

With reference to FIG. 8, selectively binding binder complex 228 to anchored analyte 226 forms tagged complex 230, e.g., to determine an identity of amino acid 209 in analyte 212 of anchored analyte 226. When analyte 212 is protein 250, amino acids in protein 250 can be sequenced using binder complex 228.

Figure 9:
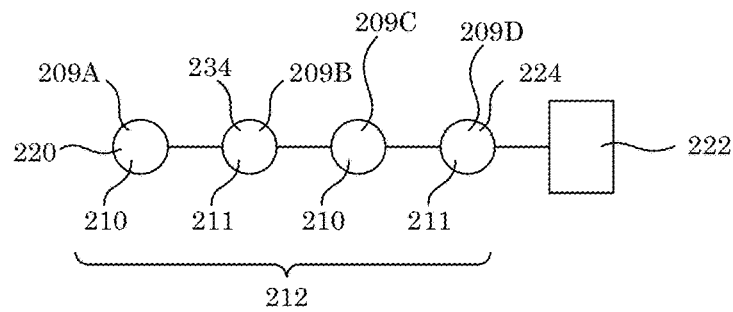
FIG. 9 shows an anchored analyte in panel A; in panel B, the anchored analyte shown in panel A after removal of an N-terminal amino acid; in panel C, the anchored analyte shown in panel B after removal of an N-terminal amino acid; and in panel D, a tagged complex with production of a taggant signal.
Figure 9:
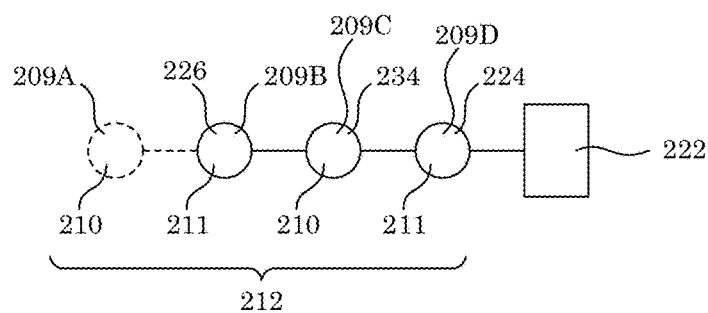
Figure 9:
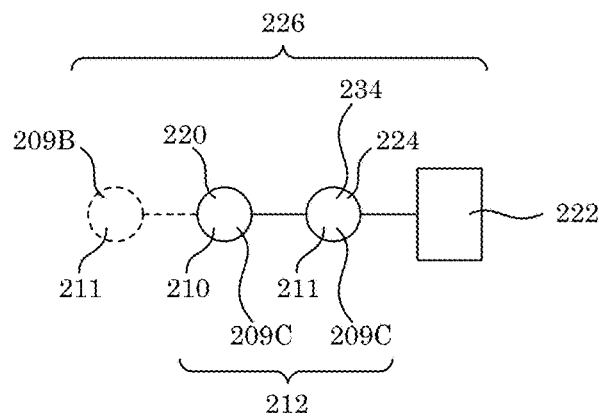
Figure 9:
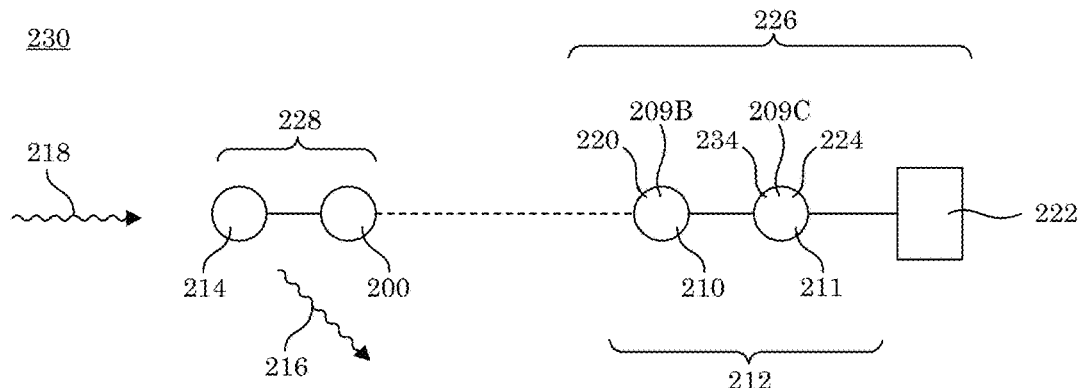

In determining a sequence of amino acids in analyte 212 in anchored analyte 226, with reference to FIG. 9, N-terminal amino acid 220 can be removed by chemical modification to expose the penultimate residue 234 as the new N-terminal amino acid 220 (panel D). Subsequent removal to expose the next penultimate residue 234 as the new N-terminal amino acid 220 can be repeated such that every new amino acid in analyte 212 can be sequentially subjected to binder complex 228 for sequencing.

Figure 10:
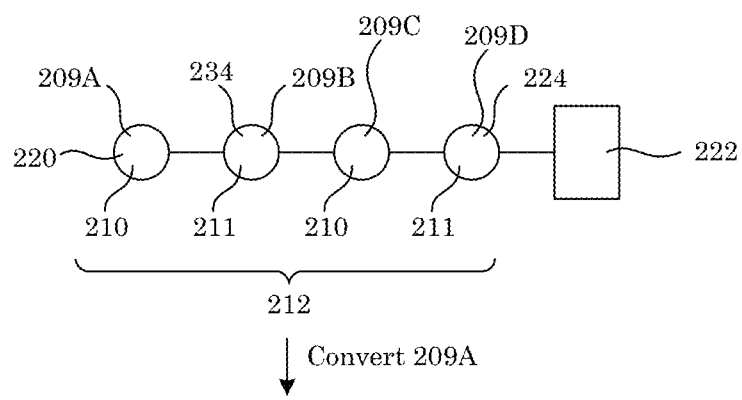
FIG. 10 shows an anchored analyte in panel A; in panel B, the anchored analyte shown in panel A after production of an inert residue from an N-terminal amino acid; and in panel C, the anchored analyte shown in panel B after production of another inert residue.
Figure 10:
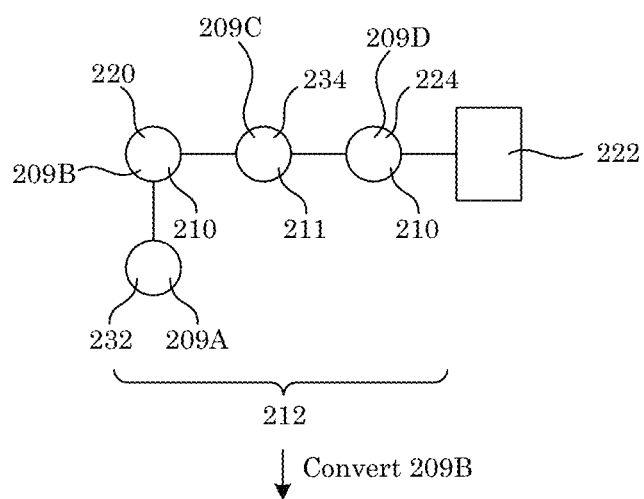
Figure 10:
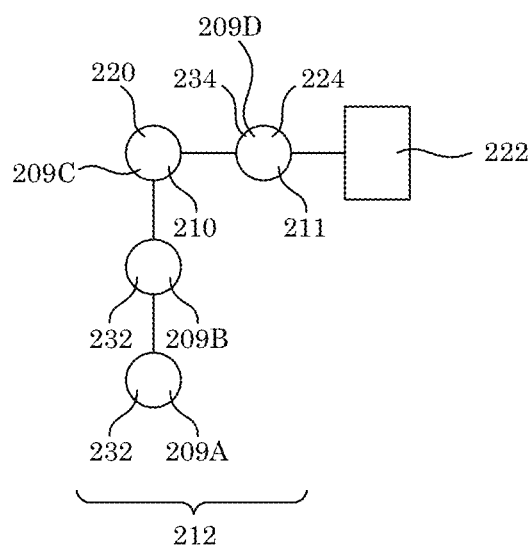

In determining a sequence of amino acids in analyte 212 in anchored analyte 226, with reference to FIG. 10, N-terminal amino acid 220 can be converted to inert residue 232. As used herein, "inert residue" refers to an amino acid that does not bind to amino acid-specific binder 200. The inert residue can be subsequently removed to expose the new penultimate residue 234 such that every new amino acid in analyte 212 can be sequentially subjected to binder complex 228 for sequencing.

Figure 11:
FIG. 11 shows, in panel A, an isolated complex that includes an amino acid-specific binder selectively bound to an analyte; in panel B, an isolated complex that includes an amino acid-specific binder selectively bound an N-terminal amino acid that is a binding amino acid in an analyte; and in panel C, an isolated complex that includes an amino acid-specific binder of a binder complex selectively bound to an N-terminal amino acid that is a binding amino acid in an analyte.
Figure 11:
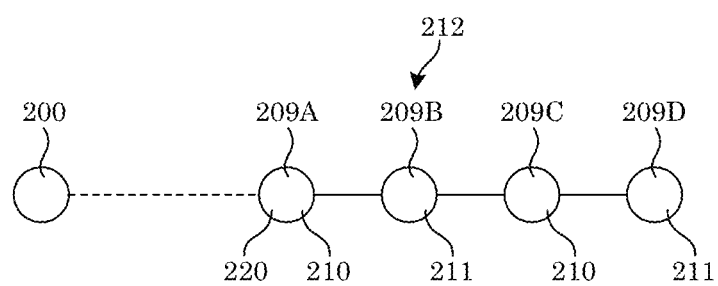
Figure 11:
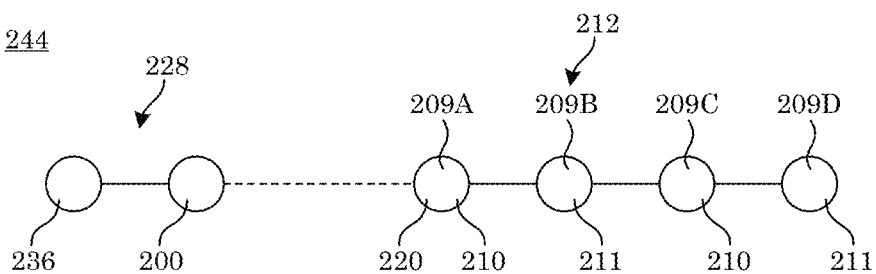

With reference to FIG. 11, selectively binding binder complex 228 to analyte 212, not in anchored analyte 226, forms isolation complex 244, e.g., to isolate analyte 212, to determine an identity of amino acid 209 in analyte 212 of isolation complex 244 and the like. Isolation complex 244 can be isolated from a heterogeneous composition containing analyte 212 using properties of isolation complex 244 such as the molecular weight. A difference in molecular weight between the isolation complex and undesired components in the composition must be great enough so that isolation complex 244 can be separated from other constituents in the composition by dialysis, chromatography, and the like.

Amino acid-specific binder 200 can be made in various ways. A process for making amino acid-specific binder 200 can include selecting a sequence for amino acid-specific binder 200 and expressing and purifying amino acid-specific binder 200 from an organism or by recombinant formation. A protein can be purified from the organism with a purification technique. Purification can include ion-exchange on a column that includes a cation-exchanger column or anion-exchanger column (e.g., diethylaminomethyl (DEAE) column), a mixed-mode ion exchanger (e.g., hydroxyapatite), or column that separates proteins based on hydrophobicity. A protein can be purified by size exclusion chromatography (e.g., gel-filtration) or in a density gradient (such as glycerol). Purification can be performed with binding to a different column that can include a specific chemical characterization of each protein. For recombinant expression in *Escherichia coli*, purification can be facilitated using a tag such as histidine, maltose binding protein (MBP), glutathione S-transferase (GST), and the like. A gene can be cloned into a pET15b vector with an additional His6-tag at an N-terminus of the protein, followed by a tobacco etch virus (TEV) protease cleavage site (MGHHHHHHENLYFQG (Sequence ID No. 13)), using the NcoI and XhoI restriction sites and expressed in BL21 *E. coli* cells. Expression from pET vector is induced with 0.5 mM IPTG when optical density at 600 nm ($OD_{600}$) reaches 1.0 absorbance units and further incubated for 6 hours at 37° C. or 16 hours at 15° C. Cells are harvested by centrifugation at 5000 g for 20 minutes, and cell pellets can be frozen. Frozen cell pellets are resuspended in a lysis buffer (e.g., 100 mM Tris-HCl, pH 8.0, 300 mM NaCl, 25 mM imidazole, or 50 mM sodium phosphate, 300 mM NaCl, or 20 mM Hepes, pH 8.0, 150 mM KCl) and sonicated on a 500 W sonicator with a C1334 probe at 20% amplitude for a time (e.g., 4 seconds on, 20 seconds off, for 90 minutes) that provides a selected total time (e.g., 15 minutes) of sonication. The lysate is centrifuged (e.g., at 20,000 g for 40 minutes) and then incubated (e.g., for one hour) that can include a chelating fast flow sepharose resin coated with nickel and pre-equilibrated in lysis buffer. The mixture is centrifuged (e.g., at 1000 g for 10 minutes) and supernatant removed, and the resin resuspended in lysis buffer that can be used to form a column. The column is washed with lysis buffer, wash buffer (e.g., lysis buffer with imidazole), and eluted with elution buffer. Protein that is eluted is subjected to dialysis into lysis buffer. Protein is removed from dialysis tubing and centrifuged, and the supernatant concentration measured by Bradford assay against a BSA standard curve. The protein is loaded onto a size exclusion chromatography column pre-equilibrated in lysis buffer. Fractions are collected from the size exclusion chromatography column and monitored at 280 nm, wherein absorption peaks are compared with a standard and analyzed by electrophoresis such as SDS-PAGE. Fractions are combined, concentrated by centrifugation with a molecular weight cutoff, such as 10 kDa, centrifuged, and measured by Bradford assay to prepare amino acid-specific binder 200.

In an embodiment, making binder complex 228 includes expressing a fusion protein of amino acid-specific binder 200 and adjunct protein 238 in an organism and purifying the fusion protein from the organism. In an embodiment, making binder complex 238 includes expressing a tagged variant of amino acid-specific binder such that it can be labeled with biotin during expression. The biotin contacts amino acid-specific binder 200 with substrate 240. In an embodiment, making binder complex 238 includes incubating the amino acid-specific binder 200 with an amine reactive chemical moiety such as NHS-ester HRP or taggant such as a fluorophore such as an NHS-ester fluorescein so that the amino-acid specific binder 200 lysine residues are linked to the fluorophore or chemical moiety.

Amino acid-specific binder 200 has numerous advantageous and unexpected benefits and uses. In an embodiment, with reference to FIG. 7 and FIG. 9, a process for selectively identifying N-terminal amino acid 220 includes providing analyte 212 including protein 250, peptide 248, amino acid 209, or a combination thereof; contacting C-terminal end 224 of analyte 212 with anchor 222; anchoring C-terminal end 224 to anchor 222 to form anchored analyte 226; contacting N-terminal amino acid 220 of anchored analyte 226 with binder complex 228, binder complex 228 include: amino acid-specific binder 200; and taggant 214 attached to amino acid-specific binder 200; selectively binding amino acid-specific binder 200 of binder complex 228 to N-terminal amino acid 220 of anchored analyte 226 when N-terminal amino acid 220 includes binding amino acid 210 to form tagged complex 230; subjecting taggant 214 of tagged complex 230 to stimulus 218; producing, by taggant 214 of tagged complex 230, taggant signal 216 in response to stimulus 218; detecting taggant signal 216; and identifying N-terminal amino acid 220 based on taggant signal 216, wherein amino acid-specific binder 200 binds selectively to binding amino acid 210.

In the process for selectively identifying N-terminal amino acid 220, providing analyte 212 includes purifying or extracting the analyte 212 from a mixture of components that may interfere with subsequent reactions. Exemplary purifications include high performance liquid chromatography (HPLC) or precipitation with ammonium sulfate. A protein can also be digested using a protease such as trypsin to create multiple peptides which can serve as analytes 212. An immobilized trypsin can be used to create multiple peptides by digestion of a protein or serum sample and purification of the peptides from the trypsin.

In the process for selectively identifying N-terminal amino acid 220, contacting C-terminal end 224 of analyte 212 with anchor 222 includes incubating or flowing the C-terminal end 224 of analyte 212 over the anchor 222.

In the process for selectively identifying N-terminal amino acid 220, anchoring C-terminal end 224 to anchor 222 to form anchored analyte 226 includes incubating the C-terminal end 224 with anchor 222 under reaction conditions to covalently link the two. Exemplary reactions would include performing an N-hydroxysuccinimide (NHS)-ester reaction to link the C-terminal amino acid sidechain lysine within analyte 212 with anchor 222 that is modified with an NHS-ester to produce an amide bond.

In the process for selectively identifying N-terminal amino acid 220, contacting N-terminal amino acid 220 of anchored analyte 226 with binder complex 228 includes incubating anchored analyte 226 and binder complex 228 in a reaction buffer for a time (e.g., from 5 sec to 30 min) for the binding reaction to occur based on a binding affinity of amino acid-specific binder 200 under a set of binding conditions (e.g., in 1×PBS at 30° C.). When N-terminal amino acid 220 is non-binding amino acid 211, the binding reaction does not occur.

In the process for selectively identifying N-terminal amino acid 220, selectively binding amino acid-specific binder 200 of binder complex 228 to N-terminal amino acid 220 of anchored analyte 226 when N-terminal amino acid 220 includes binding amino acid 210 includes incubating anchored analyte 226 and binder complex 228 in a reaction buffer for a time (e.g., from 5 sec to 30 min) for the binding reaction to occur based on a binding affinity of amino acid-specific binder 200 under a set of a binding conditions (e.g., in 1×PBS at 30° C.). When N-terminal amino acid 220 includes binding amino acid 210, the binding reaction occurs.

With reference to taggants and stimulants, signal, and detection listed in Table 1, in the process for selectively identifying N-terminal amino acid 220, subjecting taggant 214 of tagged complex 230 to stimulus 218 includes exposing tagged complex 230 on a fluorescent microscope that provides a select wavelength of light as a stimulant to produce taggant response, wherein an LED can produce excitation at 628 nm as a stimulus.

In the process for selectively identifying N-terminal amino acid 220, producing, by taggant 214 of tagged complex 230, taggant signal 216 in response to stimulus 218 includes, e.g., producing a fluorescent photon.

In the process for selectively identifying N-terminal amino acid 220, detecting taggant signal 216 includes detecting emission with a microscope that includes a detector that detects a selected wavelength of emission, e.g., 692 nm fluorescence.

In the process for selectively identifying N-terminal amino acid 220, identifying N-terminal amino acid 220 based on taggant signal 216 includes analyzing the signal response and interpreting the response based on the experimental design associated with the tagged binder complex 228. In an embodiment, the taggant is a fluorophore with a selected wavelength of emission response that provides a signal for detection through fluorescence intensity at a selected wavelength of the response to identity binding amino acid 210.

With reference to FIG. 9 and FIG. 10, the process for selectively identifying N-terminal amino acid 220, also can include removing N-terminal amino acid 220 from anchored analyte 226 so that penultimate residue 234 becomes N-terminal amino acid 220 of anchored analyte 226 by Edman degradation.

The process for selectively identifying N-terminal amino acid 220, also can include contacting N-terminal amino acid 220 of anchored analyte 226 with binder complex 228 by incubating anchored analyte 226 and binder complex 228 in a reaction buffer for a time (e.g., from 5 sec to 30 min) for the binding reaction to occur based on a binding affinity of amino acid-specific binder 200 under a set of a binding conditions (e.g., in 1×PBS at 30° C.). When N-terminal amino acid 220 includes non-binding amino acid 211, the binding reaction does not occur.

The process for selectively identifying N-terminal amino acid 220, also can include selectively binding amino acid-specific binder 200 of binder complex 228 to N-terminal amino acid 220 of anchored analyte 226 when N-terminal amino acid 220 is binding amino acid 210 to form tagged complex 230 by incubating anchored analyte 226 and binder complex 228 in a reaction buffer for a time (e.g., from 5 sec to 30 min) for the binding reaction to occur based on a binding affinity of amino acid-specific binder 200 under a set of binding conditions (e.g., in 1×PBS at 30° C.). When N-terminal amino acid 220 includes binding amino acid 210, the binding reaction occurs, and the tagged complex forms.

The process for selectively identifying N-terminal amino acid 220, also can include subjecting taggant 214 of tagged complex 230 to stimulus 218. In an embodiment, tagged complex 230 is exposed to a selected wavelength and intensity of light to excite the fluorophore. In an embodiment, subjecting taggant 214 of tagged complex 230 to stimulus 218 includes adding a chromogenic substrate. Table 1 lists a taggant, stimulant, signal, and detection for adjuncts shown in Table 2.

The process for selectively identifying N-terminal amino acid 220 also can include producing, by taggant 214 of tagged complex 230, taggant signal 216 in response to stimulus 218. In an embodiment, taggant 214 is a fluorophore that emit light as taggant response at an emission wavelength after being stimulated by an excitation wavelength as the stimulus. In an embodiment, chromogenic substrate produces chromogenic signal as when contacted by HRP as taggant 214.

The process for selectively identifying N-terminal amino acid 220 also can include detecting taggant signal 216 by methods listed in Table 2 for each taggant. In an embodiment, detection can involve a microscope with a CCD camera and selected filters in an optical system that detects a wavelength of emitted light. In an embodiment, a spectrophotometer measures absorbance at a selected wavelength to detect a chromogenic substrate. In an embodiment, a scintillation counter measures radioactivity of a radiolabeled complex.

TABLE 2

| Adjunct | Isolation Technique | Separation Property |
| --- | --- | --- |
| High molecular weight protein | Dialysis | Size |
| High molecular weight protein | Ultracentrifugation | Size |
| Substrate | Physical Separation | binding analytes are anchored |
| Protein with different solubility | Precipitation | Solubility or Molecular weight |
| Protein with different isoelectric point | Isoelectric Gradient | Isoelectric point |
| Protein with different densities | Density Gradient | Density |

The process for selectively identifying N-terminal amino acid 220, also can include identifying N-terminal amino acid 220 based on taggant signal 216 by analyzing the signal response and interpreting the response based on tagged binder complex 228. When taggant 214 is a fluorophore, the intensity and wavelength of the taggant response identifies a binding amino acid 210 due to a higher signal than non-binding amino acid 211.

With reference to FIG. 10, instead of or in combination with removing N-terminal amino acid 220, the process for selectively identifying N-terminal amino acid 220 also can include converting N-terminal amino acid 220 to inert residue 232 by performing a partial Edman degradation reaction so that phenylisothiocyanate (PITC) remains attached to the N-terminal amino acid such that a binding reaction does not occur.

The process for selectively identifying N-terminal amino acid 220, also can include converting penultimate residue 234 to N-terminal amino acid 220 when inert residue 232 is removed by continuing the Edman degradation reaction to remove the PITC.

The process for selectively identifying N-terminal amino acid 220, also can include contacting N-terminal amino acid 220 of anchored analyte 226 with binder complex 228 by incubating anchored analyte 226 and binder complex 228 in a reaction buffer for a time (e.g., from 5 sec to 30 min) for the binding reaction to occur based on a binding affinity of amino acid-specific binder 200 under a set of a binding conditions (e.g., in 1×PBS at 30° C.). When N-terminal amino acid 220 includes binding amino acid 210, the binding reaction occurs, and the tagged complex forms.

The process for selectively identifying N-terminal amino acid 220 also can include selectively binding amino acid-specific binder 200 of binder complex 228 to N-terminal amino acid 220 of anchored analyte 226 when N-terminal amino acid 220 is binding amino acid 210 to form tagged complex 230 by incubating anchored analyte 226 and binder complex 228 in a reaction buffer for a time (e.g., from 5 sec to 30 min) for the binding reaction to occur based on a binding affinity of amino acid-specific binder 200 under a set of binding conditions (e.g., in 1×PBS at 30° C.). When N-terminal amino acid 220 includes binding amino acid 210, the binding reaction occurs and tagged complex 230 forms.

The process for selectively identifying N-terminal amino acid 220, also can include subjecting taggant 214 of tagged complex 230 to stimulus 218 by exposing tagged complex 230 to a selected wavelength and intensity of light to excite the fluorophore. In an embodiment, subjecting taggant 214 of tagged complex 230 to stimulus 218 includes adding chromogenic substrate.

The process for selectively identifying N-terminal amino acid 220 also can include producing, by taggant 214 of tagged complex 230, taggant signal 216 in response to stimulus 218, e.g., by a method listed in Table 1. In an embodiment, detection can include detecting taggant response with a microscope including a CCD camera and filters in an optical system to detect a wavelength of emitted light. In an embodiment, a spectrophotometer measures absorbance at a selected wavelength to detect a chromogenic substrate. In an embodiment, a scintillation counter measures radioactivity of a radiolabeled complex.

The process for selectively identifying N-terminal amino acid 220, also can include detecting taggant signal 216. The process for selectively identifying N-terminal amino acid 220, also can include identifying N-terminal amino acid 220 based on taggant signal 216. In the process, converting N-terminal amino acid 220 to inert residue 232 can include chemically changing N-terminal amino acid 220 prior to producing inert residue 232.

Figure 12:
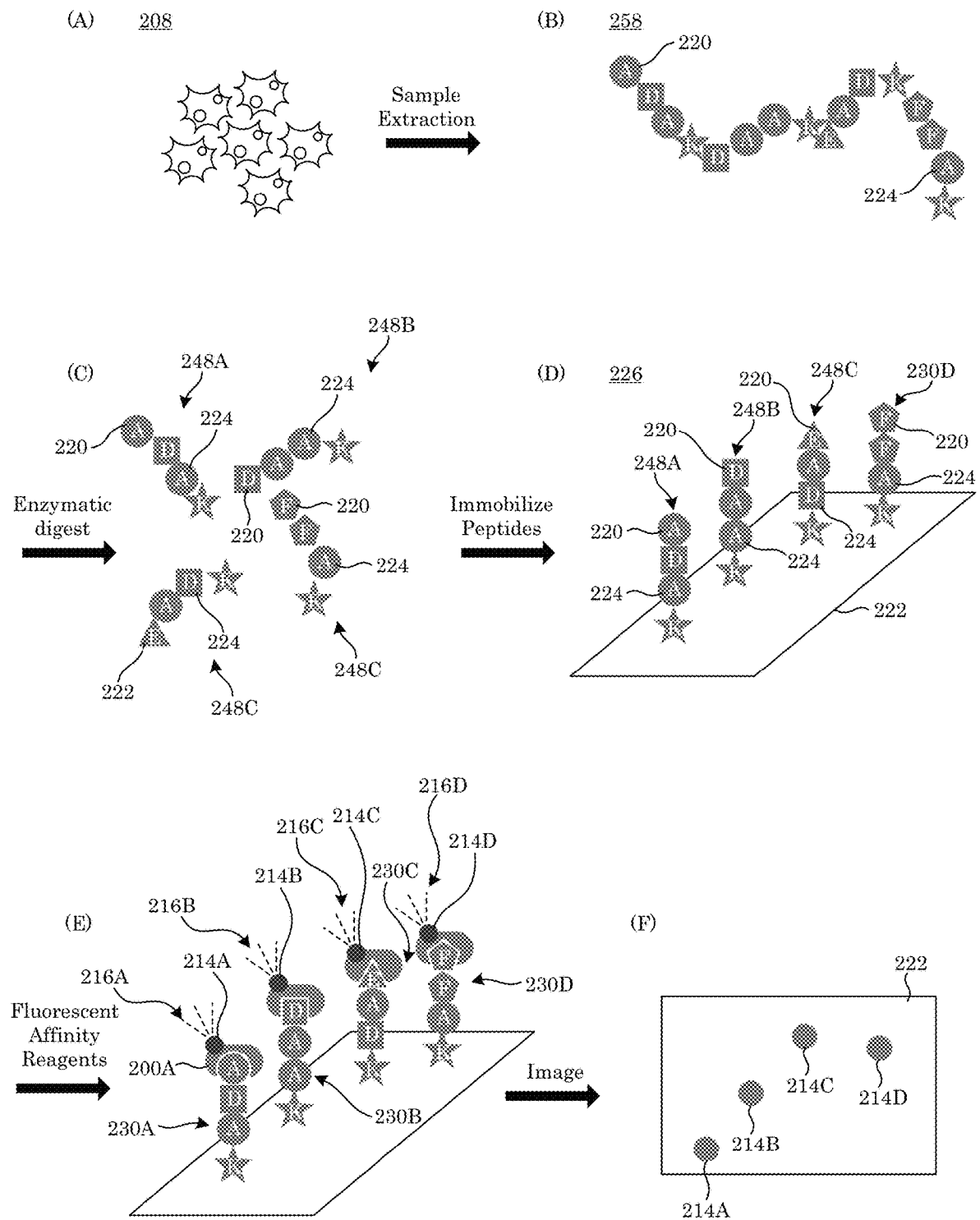
FIG. 12 shows formation of a tagged complex and detection of a taggant signal.
Figure 13:
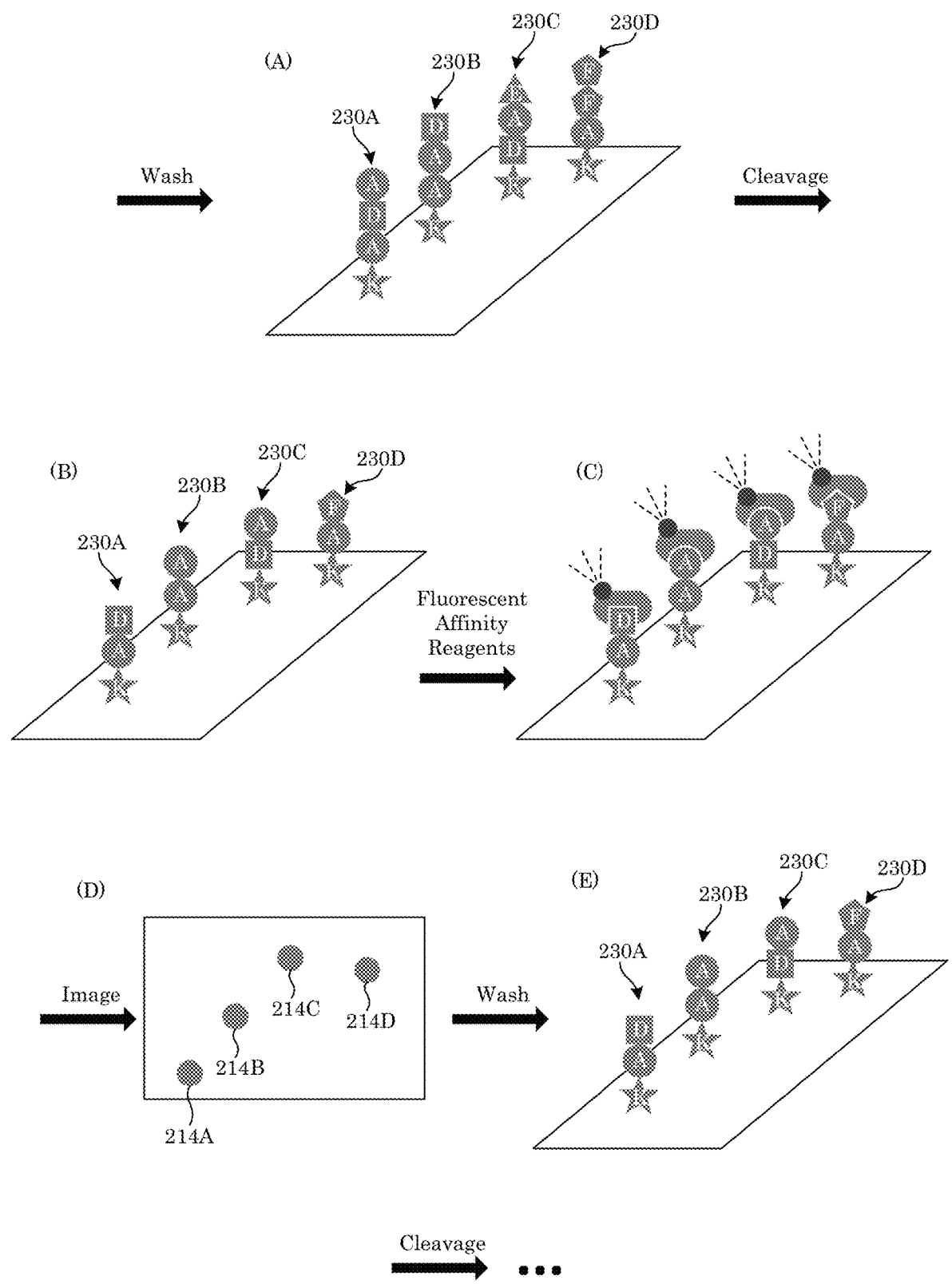
FIG. 13 shows formation of a tagged complex and detection of a taggant signal.

In an embodiment, with reference to FIG. 12 and FIG. 13, a process for sequencing protein 250 includes providing sample 208; extracting protein 250 from sample 208; enzymatically digesting protein 250 to provide a plurality of peptides 248 (e.g., 248A, . . . , 248D); forming anchored analyte 226 by immobilizing peptides 248 on anchor 222; producing tagged complex 230; detecting taggant signal 216 from taggant 214; removing binder complex 228 by washing; cleaving N-terminal amino acid 220 so that penultimate residue 234 becomes a new N-terminal amino acid 220; and repeating so that multiple repetitions of steps occur, including producing tagged complex 230; detecting taggant signal 216 from taggant 214; and removing binder complex 228 by washing; cleaving N-terminal amino acid 220 so that penultimate residue 234 becomes a new N-terminal amino acid 220 to sequence protein 250.

In the process, chemically changing N-terminal amino acid 220 prior to producing inert residue 232 can include phosphorylating free amine 252 of N-terminal amino acid 220.

In an embodiment, with reference to FIG. 11, a process for selectively isolating analyte 212 includes contacting amino acid-specific binder 200 with analyte 212 by incubating amino acid-specific binder with the analyte or analyte within a mixture in a reaction buffer for a time for binding to occur if the analyte includes binding amino acid 210. The process includes selectively binding amino acid-specific binder 200 to N-terminal amino acid 220 of analyte 212 when N-terminal amino acid 220 includes binding amino acid 210 to form isolation complex 244 by incubating them in a reaction buffer for a time for binding to occur. The process also includes separating, e.g., by dialysis, isolation complex 244 from a fluid in which isolation complex 244 is disposed to selectively isolate analyte 212.

In the process for selectively isolating analyte 212, separating isolation complex 244 from the fluid can include separating isolation complex 244 based on a size of isolation complex 244 relative to a size of other constituents in fluid by dialysis in which the isolation complex is too large to move through a pore but other constituents that the complex is being isolated from communicate through the pore. In an embodiment, the isolation complex is an immunoglobulin fusion, and analyte 212 is phenylalanine. The complex can be isolated by dialysis through, e.g., a 10 kDa molecular weight cutoff membrane. Separating can include precipitating isolation complex 244 from the fluid, ultra centrifuging in a glycerol gradient and separating the gradient fractions, and the like.

Amino acid-specific binder 200 and processes disclosed herein have numerous beneficial uses, including protein sequencing, peptide fingerprinting, and isolating amino acid analytes. Advantageously, amino acid-specific binder 200 overcomes limitations or technical deficiencies of conventional articles such as the selectivity or specificity for a particular amino acid over similar amino acids. Additionally, amino acid-specific binder 200 has higher affinity combined with high specificity than conventional approaches. As such, amino acid-specific binder 200 can discriminate amino acids for sequencing. Amino acid-specific binder 200 is specific for an N-terminal amino acid rather than an internal residue containing the same amino acid side-chain. Accordingly, amino acid-specific binder 200 determines the identity of the amino acid and a position of the amino acid in a peptide or protein. Additionally, amino acid-specific binder 200 binds a binding amino acid that is not part of a protein or peptide. To circumvent an inability to determine a position of an amino acid (N-terminal, internal, or C-terminal), conventional sequencing or fingerprinting methods rely on a loss of signal if the amino acid being detected is removed from the peptide and interpret a loss of signal at a particular iteration as an indication of position or register within the peptide. A detection scheme that relies on loss of signal is limited when another factor (such as quenching of a signaling fluorophore) also results in a loss of signal. Amino acid-specific binder 200 and tagged complex described herein overcome this limitation by adding a new amino acid-specific binder in each iteration of the sequencing process. By tagging amino acid-specific binder 200 rather than tagging the analyte directly, embodiments herein provide greater signal control and a more universal approach than conventional technology. Embodiments herein produce or detect different types of signals and include a plurality of detection schemes that provide enhanced flexibility in types of substrates and different contexts in which analyte are manipulated.

Amino acid-specific binder 200 and processes herein unexpectedly isolate analytes from a composition that includes the analyte disposed in a fluid that also includes other constituents such as amino acids, proteins, and the like. Due to the ability to anchor either the analyte or the amino acid-specific binder, the reagent can be used in many different separation processes in addition to sequencing processes.

The articles and processes herein are illustrated further by the following Example, which is non-limiting.

Example

Enhanced N-terminal Amino Acid Binding

One of the central challenges in the development of single-molecule protein sequencing technologies is achieving high-fidelity, sequential recognition and detection of specific amino acids that comprise the peptide sequence. An approach towards achieving this goal is to leverage naturally occurring proteins that function through recognition of amino (N)-terminal amino acids (NAAs). One such protein, the N-End Rule Pathway adaptor protein ClpS, natively recognizes NAAs on a peptide chain. The native ClpS protein has a high specificity albeit modest affinity for the amino acid Phe at the N-terminus but also recognizes the residues Trp, Tyr, and Leu at the N-terminal position. This Example describes directed evolution methods to select for ClpS variants with enhanced affinity and selectivity for two NAAs (Phe and Trp). Two variants of *Agrobacterium tumefaciens* ClpS protein with native residues 34-36 ProArgGlu were mutated to ProMetSer and CysProSer. In vitro surface binding assays indicate that the ProMetSer variant had enhanced affinity for Phe at the N-terminus with 7-fold tighter binding relative to wild-type ClpS, and that the CysProSer variant selectively bound to Trp over Phe at the N-terminus while having a greater affinity for both Trp and Phe. Accordingly, engineering ClpS provides an amino acid-specific binder for peptide sequencing.

Methods for high-throughput detection and quantification of single or low-abundant proteins in mixtures overcome an unmet need that spans proteomics, synthetic biology, and precision medicine. In 2014, a preliminary draft of the human proteome contained 86% of the known proteins based on predicted open reading frames (ORFs) from the genomic data available at this time. However, due to discrepancies in genomic ORF annotation in which short ORFs or genes with internal initiation sites are often miss-annotated, this number is somewhat of a moving target. As of 2017, ~18% of proteins were still considered "missing" as per Human Proteome Project metrics. While next-generation DNA sequencing technologies have enabled reductions in cost and time for nucleotide sequencing over the past decade that dramatically advanced genomic research, the field of proteomics has seen steadier, but modest advances towards throughput and completeness in proteome analysis. Similar to the effect that disruptive technologies have had on DNA sequencing, progress in proteomic research could be propelled forward dramatically with analogously disruptive advances in technologies for peptide and protein sequencing. In this respect, methods developed for oligonucleotide sequencing could provide a theoretical framework for next-generation protein sequencing technologies. However, technical challenges exist for directly interrogating amino acid residues as opposed to nucleotides. First, there are twenty possible amino acids per position in the peptide chain in comparison to only four nucleotides in an oligonucleotide. Second, post-translational modifications of amino acids, and N-terminal acetylation will ultimately need to be accounted for, just as in DNA sequencing epigenetic features such as methylation can also be detected with bisulfite sequencing. Finally, the unique chemical moieties present on each amino acid sidechain present different and perhaps more difficult challenges when it comes to distinguishing them than is the case for the different nitrogenous bases of DNA.

A natural resource for an amino acid recognition reagent is proteins that are used in cells to detect or interact specifically with a particular amino acid or post-translationally modified amino acid. For example, there are twenty tRNA synthetases, which are each highly specific for one of the twenty amino acids. Additionally, many proteases are able to uniquely identify a target amino acid and cleave before or after that residue on a peptide chain. However, a new method for detecting amino acids, in the context of sequencing, should be coupled with the ability to identify the location of that amino acid on the peptide chain. Therefore, an amino acid-binding protein, here amino acid-specific binder, is selective for an amino acid at a structurally unique chain position, such as the N-terminus of a peptide and can be a sequencing reagent. The amino acid-specific binder provides positional information of the amino acid to be directly coupled to the binding event used to detect that amino acid.

The N-End Rule Pathway functions to degrade proteins in cells as part of a regulated process for maintaining protein homeostasis. In general, the bacterial system consists of adaptor and chaperone proteins that specifically recognize the proteins to be degraded and can unfold and deliver them to a protease core for destruction, or in organisms such as yeast, which contain a ubiquitin pathway, the targeted protein may be ubiquitylated on a lysine residue and then degraded. In eukaryotes, the pathway depends on different N-terminal amino acids (NAAs) than the subset utilized in the bacterial N-End Rule Pathway. In bacteria, for example, the Clp protease that performs the degradation interacts with different chaperones divided into Class I (ClpA, ClpC, ClpD, or ClpE) or Class II (ClpX, ClpY) among different systems from proteobacterian, actinobacteria, or cyanobacteria. This pairing leads to a convenient nomenclature to describe the protease core complex (e.g., ClpAP or ClpXP). An adaptor protein in bacteria, ClpS, interacts with some Class I chaperones and is functionally an N-recognin, as it specifically recognizes the substrate to be degraded through an N-degron tag. ClpS provides a scaffold from which to develop an amino acid-specific binder (also referred to here as amino acid-binding reagent) for protein sequencing. It is a gatekeeper of the specificity of this protein degradation machinery in many organisms. ClpS and homologous domains such as one of the UBR-box (E3 ligase)N-recognin domains exist in bacteria, yeast, mammals and plants and target different N-degron tags with either type 1 (Arg, Lys, or His) or type 2 (Tyr, Phe, Trp, or Leu) destabilizing residues. The N-degron tags that ClpS proteins from bacteria recognize are sequences containing the type 2 N-terminal primary destabilizing residues. Moreover, cyanobacteria contain two different ClpS protein paralogues, which interact with different types of Clp protease cores, and exhibit different specificity. Similarly, □□proteobacteria contain two different ClpS proteins, presumably to achieve enhanced control over which N-degron containing substrates are targeted for degradation by fine-tuning the expression levels of the ClpS adaptors. In addition to wide natural variation in substrate recognition sequences, ClpS can be engineered for new specificity. For example, it was evolved for use in a "post-translational proofreading" system to detect non-standard amino acids such as p-acetylphenylalanine. Finally, the ClpS protein family has the advantages of being relatively small (MW~13 kDa) and having no native proteolytic or enzymatic activity that would be unnecessary and potentially complicating in the context of a protein sequencing application.

Based on previous studies, *Plasmodium falciparum* ClpS protein and the ClpS2 of *Agrobacterium tumefaciens* were selected as starting scaffolds for protein engineering of the amino acid-specific binder. The *P. falciparum* ClpS protein has enhanced affinity for the NAA Phe (Kd=600 nM) compared to other ClpS proteins studied to date. The second residue from the N-terminus affects binding affinity. The *P. falciparum* ClpS protein recognizes isoleucine unlike other homologs. The *A. tumefaciens* ClpS2 protein has the drawback of lower overall affinities, but the advantage of higher specificity for Phe when compared to Tyr, Trp, and Leu. Therefore, both of these proteins were chosen as starting points for a directed evolution for selecting mutants with higher affinity and selectivity for target NAAs to demonstrate the utility of the ClpS family of proteins for development of NAA binding reagents (NAABs).

With regard to plasmid construction, wild-type *P. falciparum* ClpS gene was cloned into the pET15b vector with an additional His6-tag at the N-terminus of the protein, followed by a TEV protease cleavage site, using the NcoI and XhoI restriction sites. The *A. tumefaciens* ClpS gene was amplified from genomic DNA, strain GV3101 from the C58 chromosomal background and cloned into the pET15b vector in the same manner. Both genes were cloned into the pCTCON2 vector for yeast display by amplifying the gene by polymerase chain reaction (PCR) with primers to add the NheI and BamHI sites, and then ligating this to the vector such that the gene is located to the C-terminal end of the aga2-encoding gene, separated by a factor XA cleavage site, an HA-tag and a [GGGGS (Sequence ID No. 14)]×3 spacer. There is also a C-terminal myc-tag before the stop codon. A vector was also created that contains no gene insert, but rather a SacII site and a SpeI site, so that the vector can be linearized at this site for homologous recombination.

With regard to random mutagenesis library creation, to create the random mutagenesis libraries, error-prone PCR was used. The gene encoding the ClpS protein of interest was amplified using the HA-tag for (CCAT-ACGACGTTCCAGACTAC (Sequence ID No. 15)) and T7 (TAATACGACTCACTATAGGG (Sequence ID No. 16)) primers in a reaction containing 0.2 mM dATP, 1 mM dCTP, 0.2 mM dGTP, 1 mM dTTP, 10 mM $MgCl_2$, and 0.5 mM $MnCl_2$, 1×Taq reaction buffer (20 mM Tris-HCl, pH 8.4, 50 mM KCl) without $MgCl_2$, and Taq DNA polymerase. The PCR product was used for homologous recombination, as described below. The libraries each contained at least 1 million naïve members, and greater than 50% of the colonies contained at least one mutation from the ten colonies sequenced.

With regard to *Saccharomyces cerevisiae* (yeast) transformation, EBY100 strain *S. cerevisiae* were transformed with pCTCON2 plasmids containing the wild-type ClpS genes using the Frozen EX Yeast Transformation II kit and subsequently grown on selective media as the pCTCON2 plasmid harbors the ability to synthesize tryptophan. Synthetic dextrose media supplemented with casamino acids lacking tryptophan (SD-CAA) and containing 100 μg/mL ampicillin was used to grow all the yeast used in this study. Protein surface expression was induced by resuspending the cells in synthetic galactose media supplemented with casamino acids lacking tryptophan (SG-CAA).

With regard to site-saturation library creation/homologous recombination in yeast, EBY100 *S. cerevisiae* cells were grown overnight to an $OD_{600}$ of 3 in YPD media at 30° C. This was used to inoculate a 100 mL culture of YPD to $OD_{600}$ 0.3. After 5 hours, when cells had grown to $OD_{600}$ 1.0, the cells were transferred to 50 mL conical tubes and centrifuged at 3000 g for 3 min at 4° C. The cell pellet was washed twice with 50 mL ice cold sterile water and then washed once with 50 mL ice cold electroporation buffer (1 M sorbitol/1 mM $CaCl_2$)). The cells were conditioned for electroporation by resuspending the cell pellet in 20 mL 0.1 M LiAc, 10 mM DTT and shaking for 30 min at 30 degrees. The cells were centrifuged as above and washed with 25 mL per tube of electroporation buffer before being resuspended in 200 μL of electroporation buffer to reach a final volume of about 1 mL. Cells were kept on ice until electroporation.

For electroporation, 400 μL of competent cells prepared as above were incubated with the vector and insert, in a 1:3 ratio, and kept on ice for 5 minutes. The vector used was the pCTCON2 plasmid described above containing the clpS gene of interest and digested within the clpS gene with the restriction enzyme AleI. The insert used was the error prone PCR library obtained as described above or the NNK primer (TAAGCTCTACAAGGTCATGCTGCTGAATGACGAC-TATACGNNKNNKNNKTT TGTCACCGGTGTGCT-GAAGGCCGTCTTTCGCATGAGCG, (Sequence ID No. 17)) for the site-saturation library. The cells were then transferred to a 0.2 cm electroporation cuvette and electroporated on the pre-set yeast settings (1.5 kV, 25 μF). The cells were transferred to a tube containing 4 mL of YPD media and 4 mL of 1 M sorbitol and incubated at 30° C. for 1 hour, 225 rpm. The cells were then centrifuged and resuspended in SD-CAA media and dilutions were plated to calculate library size, and the rest was grown in a flask containing 250 mL of SD-CAA media and passaged once before selections or sorting.

With regard to library selection, magnetic-activated cell sorting (MACS) and fluorescence-activated cell sorting (FACS) were performed using slightly modified protocols from the 2003 Pacific Northwest National Lab Yeast Display ScFV Antibody Library User's Manual and 2004 Methods in Molecular Biology Flow Cytometry Protocols. Yeast displaying a library of mutant ClpS proteins were grown in SD-CAA media overnight at 30° C. until the $OD_{600\ nm}$ was approximately 4.0. The yeast was used to inoculate a fresh culture at an $OD_{600\ nm}$ of 1.0 in a mixture of 80% SG-CAA/ 20% SD-CAA and incubated for 24 hours at 20° C. Approximately 109 yeast were washed and resuspended in 1 mL of Dulbecco's phosphate buffered saline containing 0.5% bovine serum albumin (PBS/BSA) (DPBS) containing 10 □M biotinylated peptide at room temperature for 1 hour. The yeast was pelleted by centrifugation at 3000 g for 2 minutes. The supernatant was decanted to remove excess peptide and the pelleted yeast resuspended with 100 μL of streptavidin coated or anti-biotin coated magnetic beads and flowed over a MACs column.

After two rounds of MACs selection, the library was sorted by flow cytometry. The cells were induced to express surface-displayed protein as described above and then incubated with biotinylated peptide in different concentrations, streptavidin-R-phycoerythrin (PE), and anti-myc AF647 overnight at room temperature. A typical reaction contained 100 μL of cells (containing approximately 106 cells), 10 □L of peptide at a concentration between 10 nM to 10 QM, and 25 μL of a master mix containing 2 μL of an anti-myc antibody, 4 μL of the SAPE (streptavidin, R-phycoerythrin conjugate—1 mg/mL) and 19 μL of PBS/BSA for each sample.

Cells were washed with PBS/BSA and sorted using a FACS Aria cytometer and collected in 1 mL of SD-CAA media. The number of cells that bound the peptide improved with each round and were sorted with sequentially lower concentrations of peptide to increase the stringency of the selection. In general, eight to sixteen colonies were sequenced from the sorted libraries after the fourth and fifth rounds of selection.

With regard to peptides, all peptides are named by indicating the first two residues, with the full sequence available in Table 3. All of the peptides had one of two sequences for the C-terminal end of the peptide, either XDEDLE (Sequence ID No. 18) or XGVECK (Sequence ID No. 19), where the N-terminal amino acid is varied on a particular peptide scaffold. The X1 G2 peptides also contained a biotin linked via the lysine side chain on the C-terminal residue. X1G2 peptides started from a lyophilized form. Peptides were resuspended in 1×DPBS and diluted to the appropriate concentration into the experiment buffer. The X1 D2 peptides were synthesized in-house on a 20 μmol scale on a peptide synthesizer with amino acid reagents and biotin resin. Synthesis resulted in a peptide with an ethylene diamine spacer and then the biotin moiety. The peptide was then cleaved from the resin using 3 mL of trifluoroacetic acid (TFA), phenol, water, and triisopropylsilane (TIPS) in an 88:5:5:2 ratio. The peptide was subsequently rinsed with ice cold ether, pelleted by centrifugation at 4500 g for 10 min at 4° C. and decanted three times. It was then dried under nitrogen overnight at room temperature and subsequently lyophilized and stored at −20° C. until resuspension in the assay buffer.

TABLE 3

| NAME | SEQUENCE |
| --- | --- |
| $X_1D_2$ | XDEDLE-biotin |
| $X_1F_2$ | XFDEDLE-biotin |
| $X_1G_2$ | XGVECK-biotin |
| WILD-TYPE (WT) | *A. tumefaciens* ClpS2 [$Pro_{34}$ $Arg_{35}$ $Glu_{36}$] |
| VARIANT 1 (V1) | *A. tumefaciens* ClpS2 [$Pro_{34}$ $Met_{35}$ $Ser_{36}$] |
| VARIANT 2 (V2) | *A. tumefaciens* ClpS2 [$Cys_{34}$ $Pro_{35}$ $Ser_{36}$] |
| VARIANT 3 (V3) | *A. tumefaciens* ClpS2 [$Cys_{34}$ $Ser_{35}$ $Trp_{36}$] |

With regard to protein purification, the wild-type and mutant ClpS proteins were expressed in BL21 *Escherichia coli* cells. Expression of wild-type and ProMetSer mutant proteins was induced with 0.5 mM IPTG when the $OD_{600\,nm}$ reached 1.0 and incubated for 6 hours at 37° C. The cells expressing the CysProSer and CysSerTrp mutants were removed from the 37° C. incubator and cooled to 15° C. when the $OD_{600\,nm}$ reached 0.5, then induced with 0.5 mM IPTG when the $OD_{600\,nm}$ reached 1.0 and grown for 16 hours at 15° C. The cells were harvested by centrifugation at 5000 g for 20 minutes, and the cell pellets frozen for future use.

Frozen cell pellets were resuspended in lysis buffer (100 mM Tris-HCl, pH 8.0, 300 mM NaCl, 25 mM imidazole,), and sonicated with a probe at 20% amplitude for 4 seconds on, 20 seconds off, for 90 minutes, which results in 15 minutes total sonication time. The lysate was centrifuged at 20000 g for 40 minutes and then incubated for one hour with chelating fast flow sepharose resin coated with nickel and pre-equilibrated in lysis buffer. The mixture was centrifuged at 1000 g for 10 minutes and then the supernatant removed, and the resin resuspended in 5 mL lysis buffer and used to form a column. The column was then washed with 10 column volumes (CVs) of lysis buffer, and then 5 CVs of wash buffer (100 mM Tris-HCl, pH 8.0, 300 mM NaCl, 75 mM imidazole,), before eluting with 5 CVs of elution buffer (100 mM Tris-HCl, pH 8.0, 300 mM NaCl, 250 mM imidazole). The eluted protein was then dialyzed using 10 kDa molecular weight cutoff (MWCO) dialysis tubing into 50 mM Tris-HCl, pH 8.0, 300 mM NaCl, 1 mM DTT, 5% glycerol. Each dialysis was performed for >12 hours, for a total of 3 times. The protein was removed from dialysis tubing, centrifuged 40 minutes at 20,000 g, and the supernatant concentration measured by Bradford assay against a BSA standard curve. The protein was then loaded onto a S200 26/60 size exclusion chromatography column pre-equilibrated in 2CV of 50 mM Tris-HCl, pH 8.0, 300 mM NaCl, 5% glycerol, 1 mM DTT. 5 mL Fractions were collected and tracked at 280 nm; peaks were compared with a gel filtration standard and further analyzed by SDS-PAGE. Fractions were combined, concentrated by ultra-centrifugation with a 10 kDa MWCO, centrifuged for 40 minutes at 20,000 g, and measured by the Bradford assay.

The thermal stability of the variants was assessed. Each variant was loaded in 3×PBS at approximately 1 mg/mL concentration in capillary tubes and the intrinsic protein fluorescence recorded at 330 nm and 350 nm while heating the sample over a 35-95° C. at a rate of 30° C. per minute.

With regard to yeast or peptide pull-down assay, a colorimetric pull-down assay was used to screen the FACS selected library variants with different peptide substrates in a high-throughput manner and determine the optimal candidates for in vitro characterization. Yeast displaying the library variants of interest were grown to saturation in SD-CAA media and transferred to SG-CAA media for surface expression at 20° C. for 24 hours. The cultures were pelleted at 3000 g for 2 minutes and washed with PBS, 0.5 mg/mL BSA, 0.1% ELISA buffer and diluted to OD600 nm=2.5. A UV-transparent 96-well flat-bottomed polystyrene plate was pre-blocked with 1 mg/mL BSA and washed with ELISA buffer. 10 μL of diluted cells were added to the wells and mixed with 90 μL of 1 μg/mL biotinylated peptide substrate in ELISA buffer. The mixture plate was incubated in a benchtop orbital shaker for 1 hour, then centrifuged at 3000 g to pellet the yeast cells bound to peptide and wash the excess peptide away by washing three times with 100 μL of buffer. The cells were resuspended in 100 μL of buffer with 1 μg/mL of streptavidin-HRP. Incubation and wash steps were repeated. Cells were resuspended in a final volume of 50 μL buffer and 50 μL of 1x tetramethylbenzidine was added to the wells. Reactions were incubated for 20 minutes at room temperature for oxidation of the TMB by horseradish peroxidase (HRP), which produces a blue coloration. Reactions were then quenched by adding 100 μL of 1M HCl, which produces a yellow color that can be measured by the absorbance at 450 nm. The intensity is a function of the amount of streptavidin-HRP pulled down by interaction with the yeast cells, facilitated by biotinylated peptide binding to surface-expressed ClpS.

Each sample was measured in triplicate within the same row of the 96 well plate, allowing for four ClpS/substrate pairs per row, with the standard deviation of Abs 450 nm taken as the error. Fluid was added to rows using a 12-channel hand pipette. In assays, when testing a single library variant against a panel of peptides, wells 1 through 3 were empty as a check for artifacts; peptide was added to wells 4 through 6; wells 7 through 9 had peptide and uninduced yeast, and wells 10 through 12 had peptide and yeast. As the background in lanes 1 through 9 showed no increase in background absorbance from the peptide or media, the data displayed here is the average and standard deviation of lanes 10 through 12, except for the data labeled "no yeast", which is lanes 4 through 6.

With regard to surface plasmon resonance (SPR), SPR data was collected by loading a streptavidin chip with the target biotinylated peptides in each of the four channels, and then flowing the protein over the chip at each concentration for 180 seconds before washing with 50 mM Tris-HCl, pH 8.0, 300 mM NaCl, 1 mM DTT, 5% glycerol buffer for 180 seconds. The SPR assays for all variants were performed under the above optimized buffer conditions to obtain the greatest binding activity, as the activity and stability of ClpS is pH, and NaCl concentration dependent. Additionally, the wild-type and mutant proteins purify as dimers that can be disrupted by the addition of DTT, indicating they are likely disulfide-linked with different homologs of ClpS having different propensities for dimerization. The four channels were used such that the negative control peptide (A1G2) was in channel 1, F1G2 in channel 2, W1G2 in channel 3, and Y1G2 in channel 4. The negative control peptide channel was used as a baseline for subtraction, which accommodates both any non-specific binding and refractive index change. A steady state response at each concentration was plotted and fit to calculate the KD, while the resonance units vs. time was used to calculate a $k_{off}$ for each mutant protein with each peptide.

Figure 14:
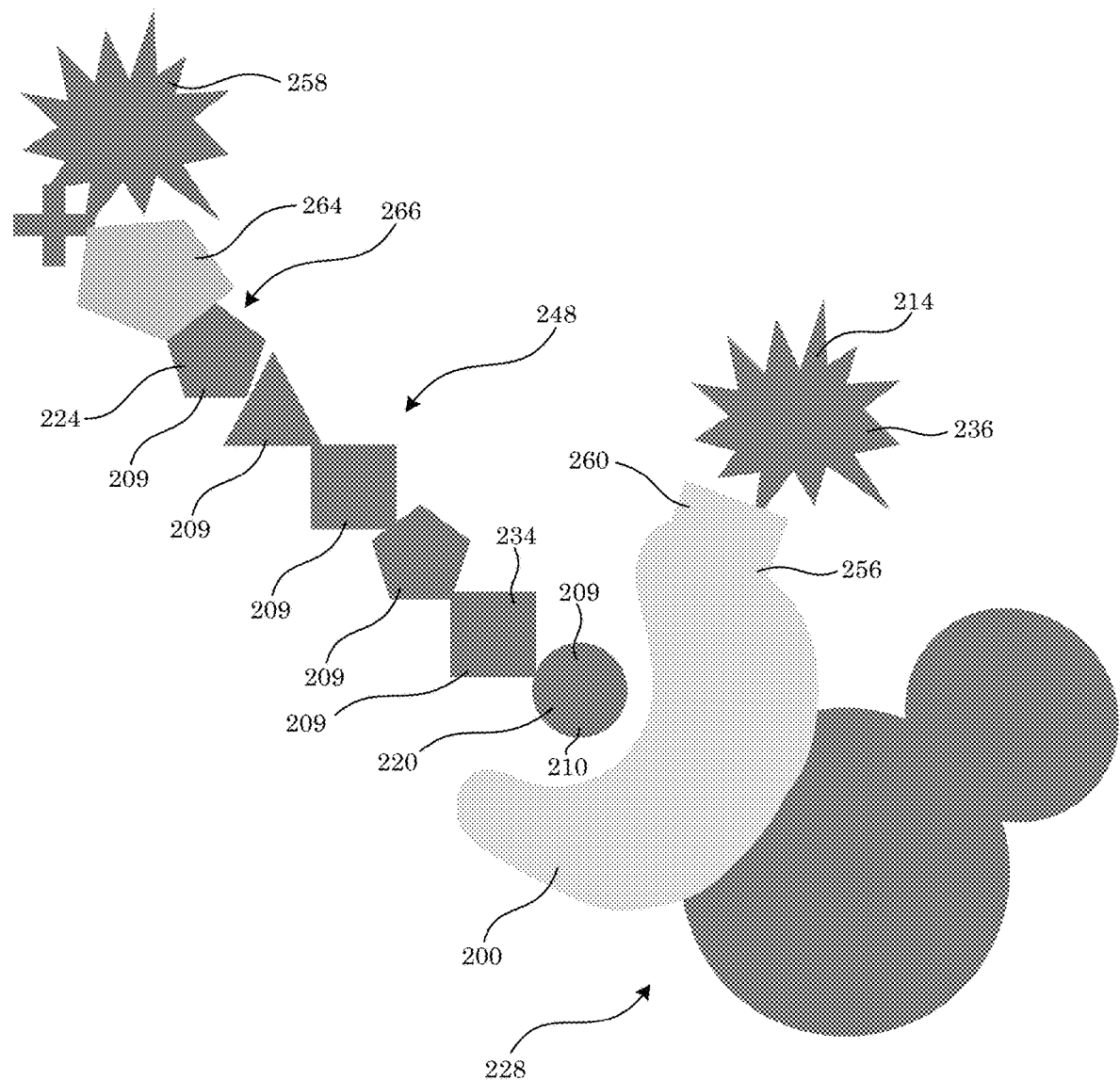
FIG. 14 shows a fluorescent labeling for detection of peptide binding during flow cytometry, wherein myc tag 260 is detected with fluorescent label taggant 214 on anti-myc antibody 256. Peptide 248 is detected using streptavidin-PE 258 that binds biotin 264 attached to C-terminus 224 of peptide 248.
Figure 15:
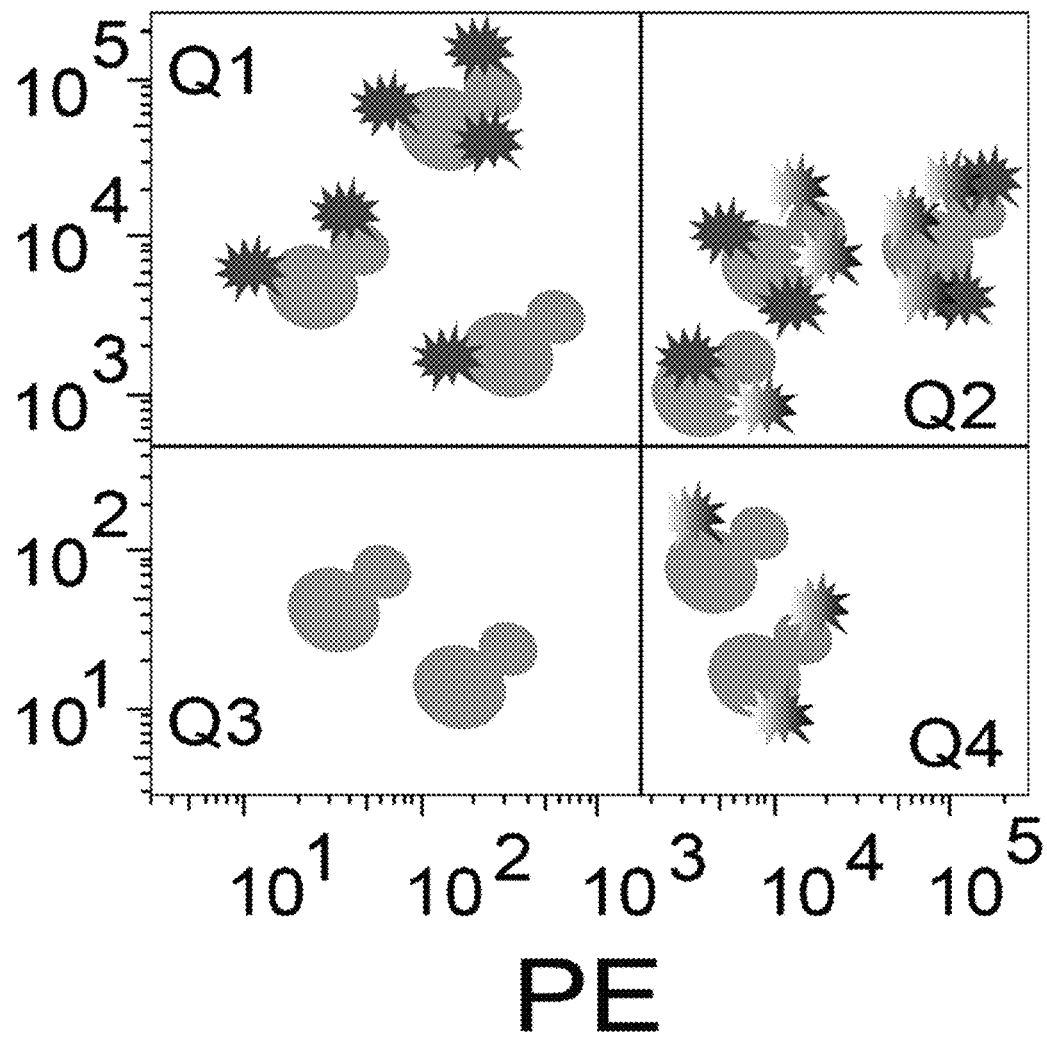
FIG. 15 shows an expected flow cytometry result for yeast that displays a non-binding protein in quadrant 1 (Q1), yeast that binds the peptide in Q2, yeast that does not display the protein in Q3, and yeast that exhibits non-specific binding to the peptide in Q4.
Figure 16:
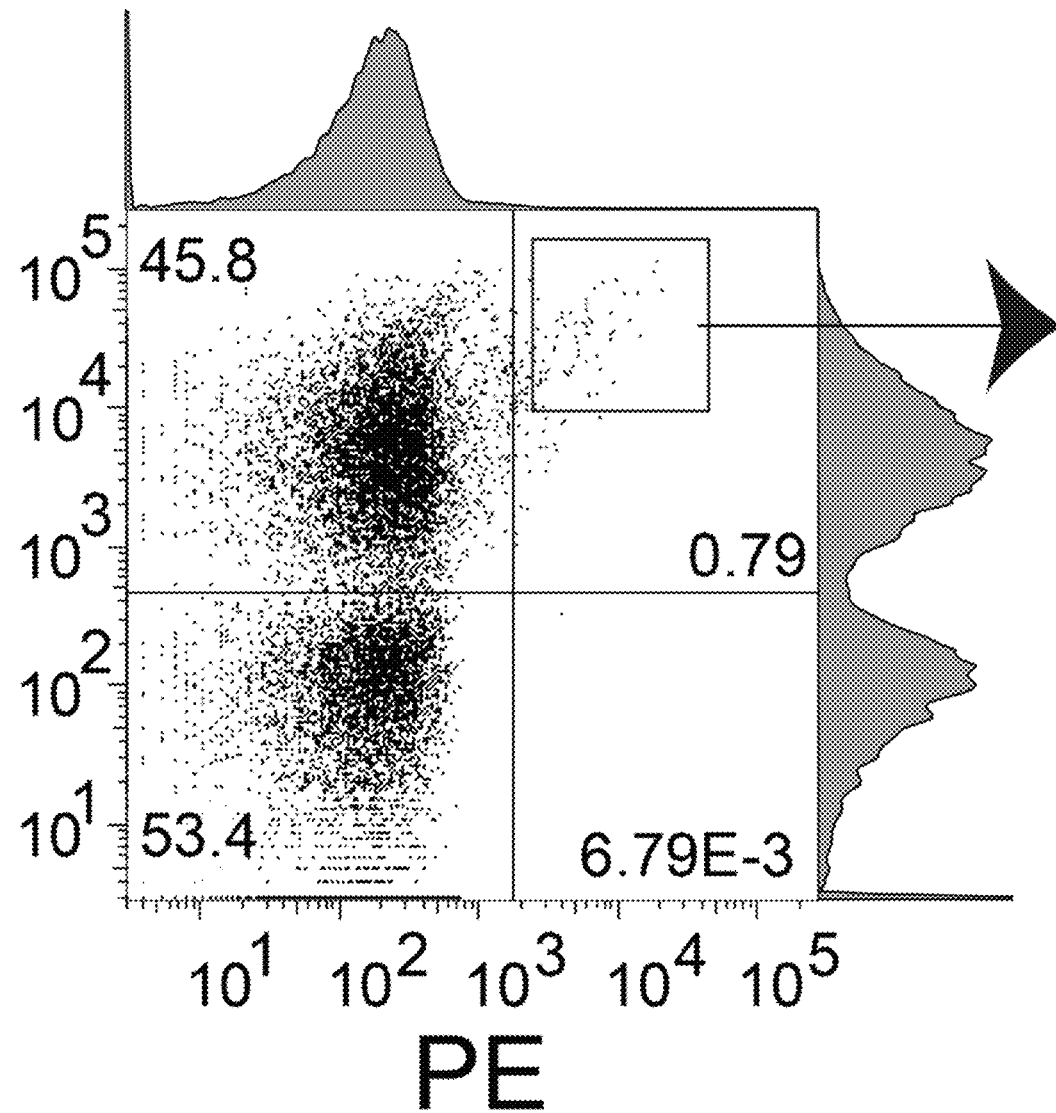
FIG. 16 shows a graph of fluorescent taggant fluorescence versus phycoerythrin (PE) fluorescence for flow cytometry plots displaying increased PE fluorescence seen in each round after 3 rounds of selection of a library against a Phe peptide, wherein the square and arrow in Q2 correspond to cells carried on to a next round of sorting after outgrowth.
Figure 17:
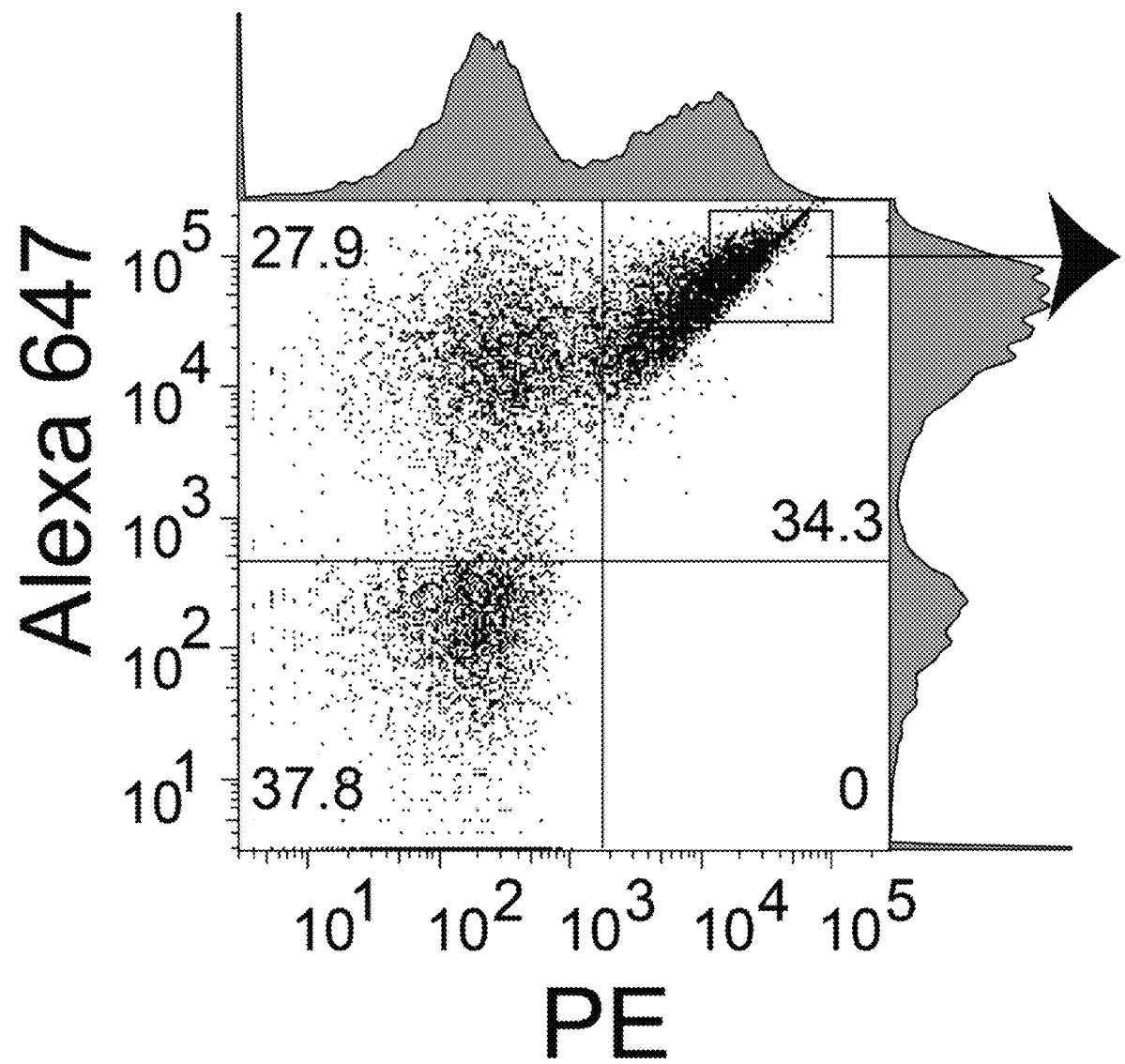
FIG. 17 shows a graph of fluorescent taggant fluorescence versus PE fluorescence for flow cytometry plots displaying increased PE fluorescence seen in each round after the data shown in FIG. 16 and an additional 3 rounds of selection of a library against a Phe peptide, wherein the square and arrow in Q2 correspond to cells carried on to a next round of sorting after outgrowth.
Figure 18:
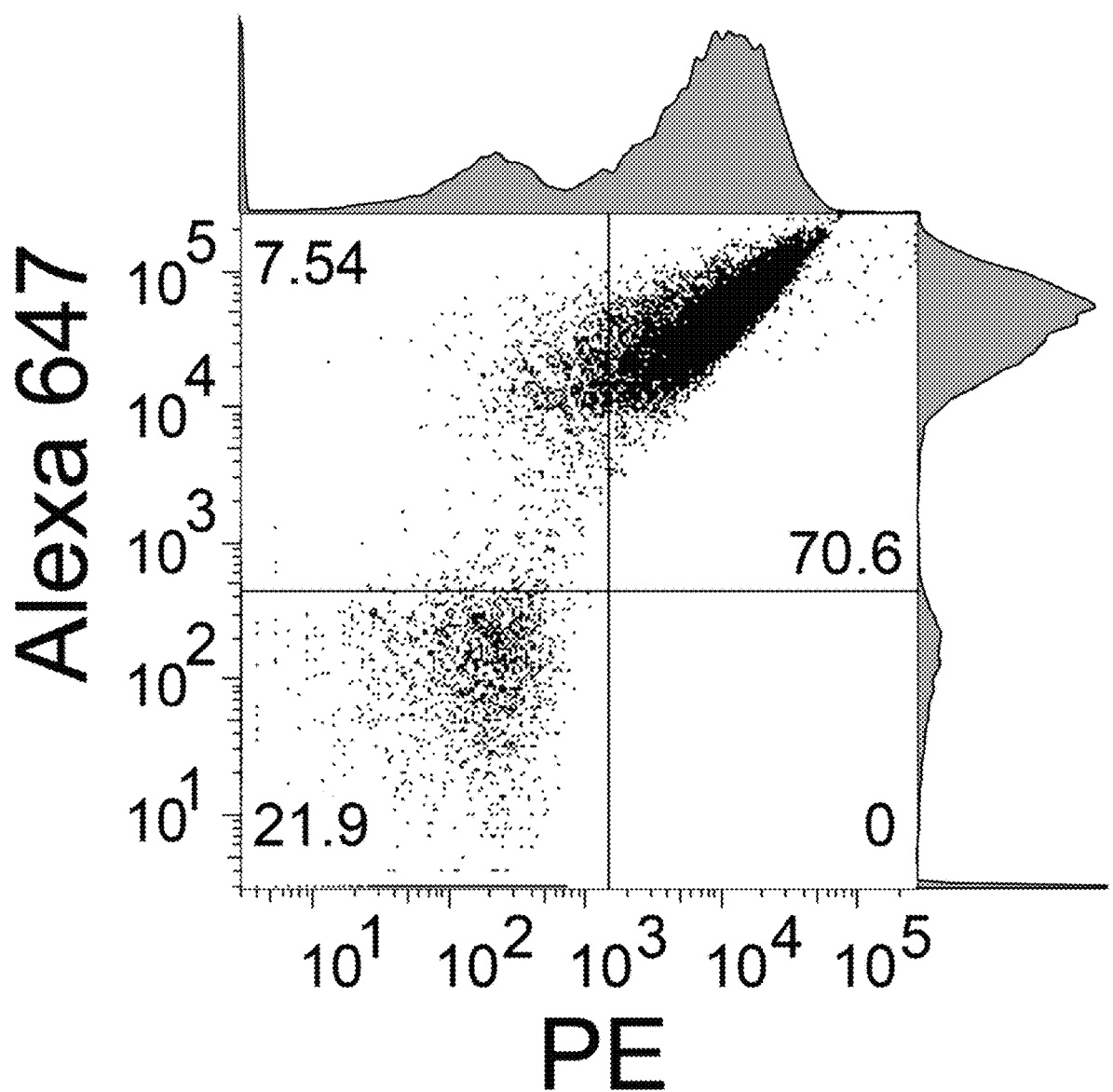
FIG. 18 shows a graph of fluorescent taggant fluorescence versus PE fluorescence for flow cytometry plots displaying increased PE fluorescence seen in each round after the data shown in FIG. 17 and an additional 3 rounds of selection of a library against a Phe peptide.

With regard to directed evolution of ClpS, random mutagenesis and screening was used to select proteins with higher affinity binding to the target NAA. In subsequent steps, specific residues were determined from initial screens with a targeted mutagenesis step. An error-prone PCR approach was applied to broadly and randomly mutagenize both the P. falciparum clpS gene and the A. tumefaciens clpS2 gene. We then performed homologous recombination into a yeast display vector such that the gene of interest was fused to the C-terminal end of the aga2 gene for display. The displayed proteins also contained a C-terminal myc-tag that could be used for detection as shown in FIG. 14, where a fluorescent label (commercially available as ALEXAFLUOR647) labeled antibody could bind to the C-terminal myc-tag, while successful binding of the ClpS protein variant to a biotinylated peptide with the appropriate N-terminal amino acid was monitored by detection with a fluorescently-labeled streptavidin. Using FACS, we assessed the affinity of each mutant for the N-terminal amino acid on the target peptide based on which quadrant the fluorescent signal fell into as shown in FIG. 15. If the AlexaFluor647 signal is high, the full-length protein is accessible on the yeast surface for the antibody to bind and the cell will appear in Q1 or Q2. If there is also a high fluorescence signal along the x-axis (streptavidin-PE) then the peptide is presumably bound to the protein variant, and the signal will appear in Q2. As shown in FIG. 16, a naïve library will contain a mixture of yeast cells, some of which do not express full-length variants and fall into Q3. Some of the variants will be expressed but not bind the peptide, as in Q1, and a small percentage of the library will contain variants which bind the peptide of interest as in Q2. For a given library, the top 5% to 10% of cells, those in the 2nd quadrant which express mutant ClpS proteins that bind the peptide of interest (in this case F1 D2), were sorted and grown in selective media. In the second (FIG. 17) and third (FIG. 18) rounds, the cells that were selected from the first or second rounds, respectively, were sorted again until the majority of the library members had an affinity for the peptide of interest. As illustrated, the percentage of cells displaying a protein that bound the peptide did increase with each round of selection. One representative library selection is shown in FIG. 14-FIG. 18 where three rounds of selection were performed for this library. This process was repeated multiple times after the creation of each new mutant library. The sequence and corresponding nomenclature for the target peptides used in selections and screens is given in Table 3, where X stands for any amino acid. Sequencing analysis of the individual clones from the final round of selection of the first error-prone PCR library for each protein indicated that there was indeed a hotspot of substituted residues corresponding to residues 122-124 in the P. falciparum protein, and the homologous residues, 34-36 in the A. tumefaciens protein. The mutated residues are highlighted in yellow in FIG. 19 and the hotspot residues are boxed. FIG. 19 was generated using the ESPript 3.0 web utility. These same residues were mutated in many of the constructs that showed altered and improved affinity for the various targeted peptides. These residues are in a flexible loop near the opening of the peptide binding site on ClpS based on an available crystal structure from P. falciparum (PDB: 4O2X) and the structure of A. tumefaciens bound to phenylalaninamide (PDB:4YJX). Based on this observation, we created a second library of the A. tumefaciens ClpS2 in which these three residues were mutated to all 20 amino acids (a theoretical library size of 8000 constructs). This new library was further screened against either an F1 peptide or a W1 peptide, and after 4 rounds of selection the hits were again sequenced and characterized. The variants that were chosen for characterization are given in Table 3 with the three residues that were mutated from the wild-type sequence listed. Some proteins behaved well in the yeast displayed context but were not amenable to E. coli expression and purification, while others were easily purified from E. coli but had high background in the yeast-display format, which was traced to non-specific binding to the streptavidin-HRP. Therefore, two of the variants (V2 and V3) were subjected to the pull-down assay, and two variants (V1 and V2) after expression and purification of the proteins from E. coli in SPR experiments.

Figure 20:
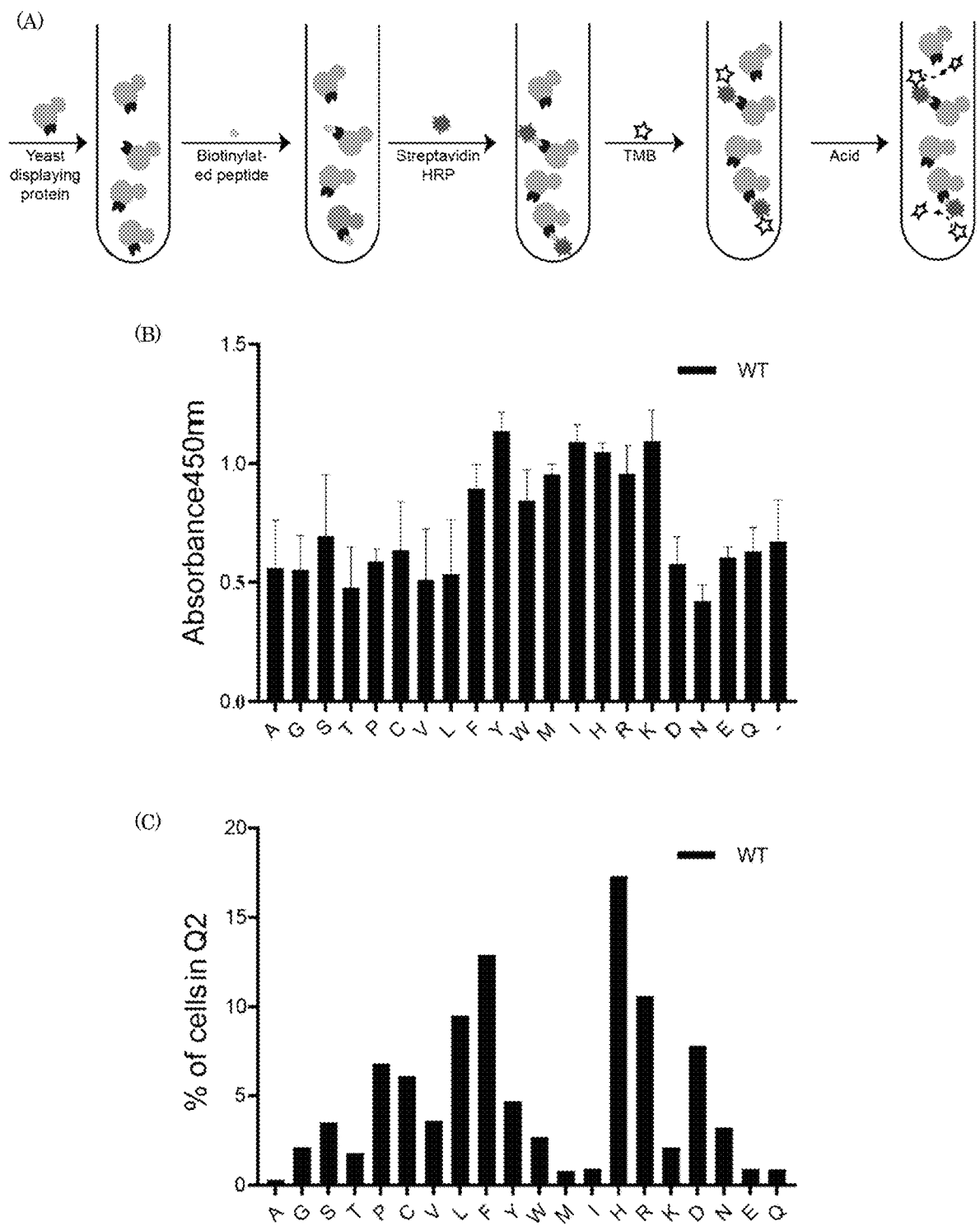
FIG. 20 shows, in panel A pull-down assay workflow for incubation of yeast with a peptide of interest, centrifugation and washing to remove unbound peptide, labeling with the streptavidin-horseradish peroxidase (HRP), followed by incubation with tetramethylbenzidine (TMB) substrate and acid quenching that resulted in a yellow color change that was quantified in each well of a 96-well plate; panel B shows a graph of absorbance at 450 nm versus amino acid, wherein absorbance at 450 nm correlates with a number of yeasts bound to the peptide. Error bars are for three replicate measurements of one biological sample; panel C shows a graph of percentage of cell in Q2 versus amino acid.

With regard to characterization of yeast-displayed ClpS mutant proteins, we designed a pull-down assay to screen the FACS-selected hits against many different NAA containing peptides in high-throughput. As shown in panel A of FIG. 20, yeast displaying a particular mutant ClpS protein were incubated with a panel of C-terminally biotinylated peptides containing different NAAs. Samples were then centrifuged, washed, and incubated with streptavidin-HRP and TMB substrate, followed by acid addition to quench the reaction. This was used to identify the yeast displaying proteins with differing specificity or affinity towards those peptides as compared to the wild-type protein warranting further characterization. Two protein variants from the FACS selection were characterized with a full panel of 20 peptides to assess whether the affinity for other NAA peptides was inadvertently changed. V2 had an improved affinity for the W1 G2 peptide compared to the wild-type, as determined via flow cytometry of the yeast displaying these proteins and via the pull-down assay described above. Conversely, V3 displayed increased affinity for the F1G2 peptide and higher selectivity towards the F1G2 peptide as compared to other NAAs. Neither mutant protein had any undesirable off-target affinity towards any NAA that was not already recognized by the wild-type protein, with one exception. V2 has an increased affinity towards Leu, which the wild-type A. tumefaciens ClpS protein does not bind. However, an affinity for Leu is exhibited by other ClpS homologs. Therefore, V2 appears to have re-gained some of the canonical binding activity of the ClpS protein family with respect to leucine. In fact, the affinity for every other residue besides the canonical (Phe, Trp, Tyr, Leu) binding residues was either the same or reduced compared to the wild-type. Our pull-down assay also indicated, for the first time, that the wild-type ClpS2 protein has some binding activity towards Met, His, Arg, and Lys at the high concentrations used in the assay. The His and Arg binding was also confirmed via flow cytometry. Some differences between the observed binding for a particular residue is likely due to the different concentrations and format used for the assay and whether that was above or below the kD for binding to that residue. Finally, the pull-down assay shows the wild-type protein does bind Ile, which disagrees with the flow cytometry assay. From our pull-down assay, we confirm lack of binding to Val and Ala, and add the remaining amino acids to the non-binding category.

Regarding characterization of the ClpS mutant protein binding kinetics, for peptide sequencing via some recently proposed methods reagents can bind peptides affixed to a surface. Two *A. tumefaciens* ClpS2 protein variants (V2, described above, and V1) were expressed and purified from *E. coli*. V2 was not as thermally stable as the wild-type and V1. The binding properties of each variant were analyzed using surface plasmon resonance (SPR). Since the SPR chip has four channels, we chose three peptides ending in the residues that are the most commonly recognized by the wild-type ClpS proteins (Phe, Trp, Tyr) and a negative control (Ala). The summary of the SPR data is displayed in Table 4, where the steady state values of the KD are calculated from the experiments performed using concentrations ranging from 0 to 50 μM of protein for each variant.

TABLE 4

| $K_D$ (μM) | | | |
|---|---|---|---|
| Variant | Phe | Trp | Tyr |
| WT | 13.0 ± 0.6 | 18.4 ± 0.4 | 63.0 ± 4.0 |
| V1 | 1.8 ± 0.4 | 13.1 ± 1.3 | 11.6 ± 1.2 |
| V2 | 3.7 ± 0.3 | 2.8 ± 0.3 | 36.1 ± 4.4 |
| Selectivity for Phe | | | |
| Variant | Phe/Phe | Phe/Trp | Phe/Tyr |
| WT | 1.0 | 0.71 | 0.21 |
| V1 | 1.0 | 0.14 | 0.16 |
| V2 | 1.0 | 1.32 | 0.10 |
| Selectivity for Trp | | | |
| Variant | Trp/Phe | Trp/Trp | Trp/Tyr |
| WT | 1.42 | 1.0 | 0.29 |
| V1 | 7.28 | 1.0 | 1.13 |
| V2 | 0.76 | 1.0 | 0.08 |
| Selectivity for Tyr | | | |
| Variant | Tyr/Phe | Tyr/Trp | Tyr/Tyr |
| WT | 4.86 | 3.43 | 1.0 |
| V1 | 6.43 | 0.88 | 1.0 |
| V2 | 9.82 | 12.91 | 1.0 |

Figure 21:
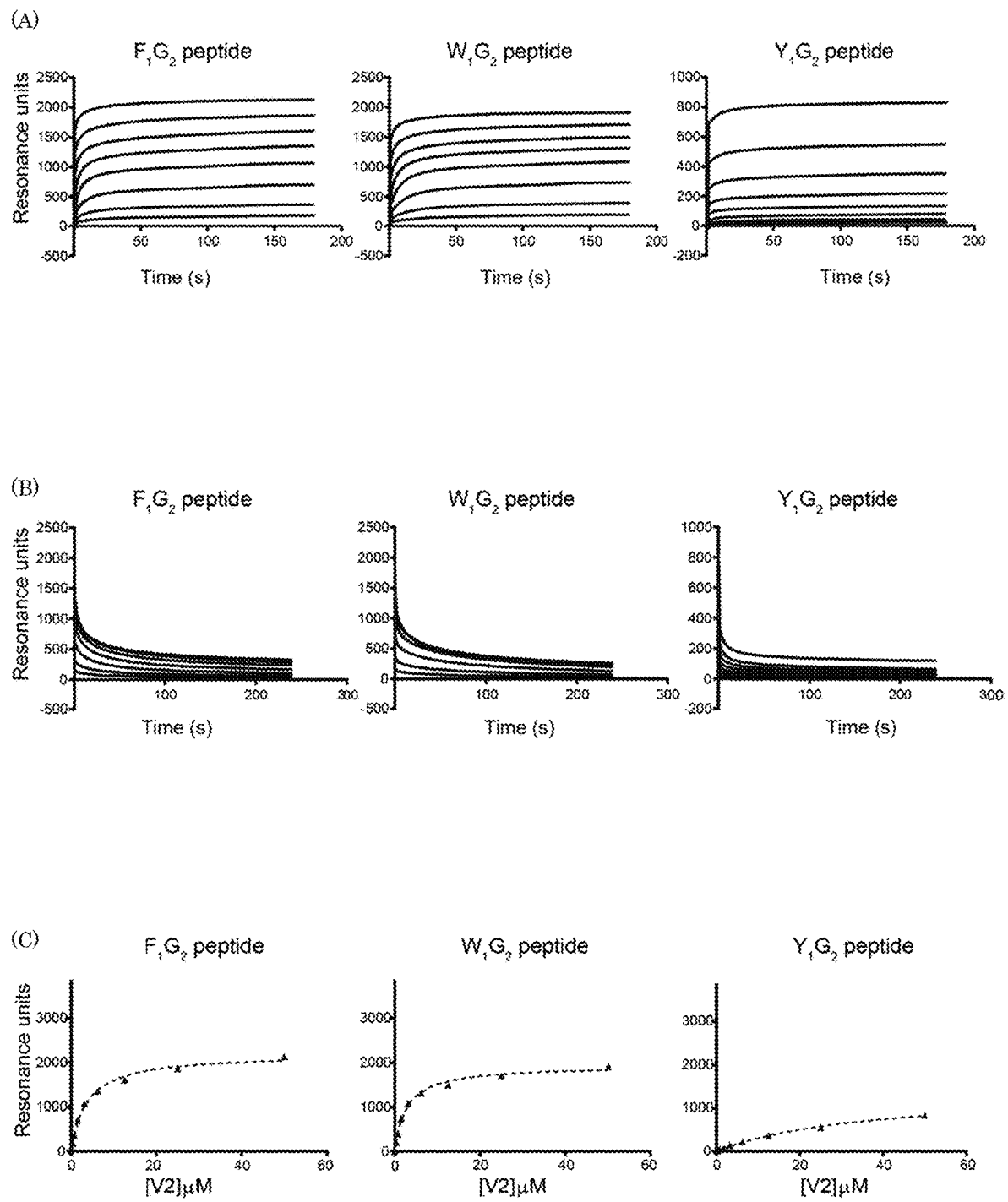
FIG. 21 shows, in panel A association curves from an SPR performed with the peptide of interest attached via biotin to a streptavidin chip and the ClpS2 variant protein in solution at concentrations 0, 0.39, 0.78, 1.56, 3.13, 6.25, 12.5, 25, and 50 QM; panel B shows dissociation curves for the same SPR measurements, and panel C shows a steady-state response from SPR association curves plotted versus concentration of each mutant for three different peptides, wherein dashed lines are fits used to calculate stead-state KD.

The association curves for V2 with each peptide ending in Phe, Trp, or Tyr, are given in panel A of FIG. 21. The dissociation curves are shown in panel B of FIG. 21, and the steady state plot calculated from the plateau of the association curve for each concentration is given in panel C of FIG. 21. Significantly, a 6.6-fold decrease in the KD for W1G2 peptide was observed for V2, compared to the wild-type protein, as determined by SPR with the peptide attached to the surface and the protein in solution. A 3.5-fold improved KD was observed for V2 with the F1 G2 peptide as well. This data supports the trend observed from the pull-down assay that also showed increased binding affinity, compared to wild-type, to Phe, Trp, and Tyr. Via the SPR assay, V1 has little change in its affinity for tryptophan and had improved 7.2-fold in affinity for the F1G2 peptide, and 5.5-fold for Y1G2. Thus, the ClpS2 variants have increased affinity for either Phe or Trp. Due to the overall increases in affinity compared to the wild-type proteins it is difficult to discern the change in selectivity of the mutant proteins. Therefore, the binding affinity for each variant with respect to one peptide was divided by the affinity for each of the other peptides to give a relative specificity factor displayed in the three lower panels of Table 4. If the specificity factor is less than 1, the protein has higher affinity for a different NAA than the one tested in that panel, and vice-versa if the specificity factor is greater than 1. Presenting the binding data in this way clearly shows, as expected, that the wild-type protein has a modest specificity for N-terminal Phe. Although V2 is improved in KD for both peptides with N-terminal Phe and Trp, V2 is more specific for Phe over Trp than the wild-type protein. Additionally, V1 is more specific for N-terminal Trp than for Phe. It is worth noting that residue 35 (mutated from Arg to Met in V1) is homologous to the *E. coli* ClpS1 residue M40, which is considered to be a gatekeeper residue that when mutated to Ala allows non-canonical NAAs such as Val to fit in the binding pocket. It is evolutionarily conserved as a Met in bacterial ClpS1 proteins but is conserved in eukaryotic ClpS1 proteins as an Arg residue and is sometimes found as Glu or Phe in other ClpS1-like and ClpS2 proteins. In the *Arabidopsis thaliana* ClpS1 protein the Arg residue at this position was replaced with Met in a back-to-bacterial consensus mutant and the canonical bacterial binding affinity was recapitulated. Thus, the V1 binding pocket is more similar to the bacterial ClpS1 proteins than its parent *A. tumefaciens* ClpS2 protein in this respect.

The SPR experiment gives steady-state KD and on- and off-rates. A contribution to improved KD resulted from a slower off-rate for the mutant proteins. From SPR sensorgrams shown panel B of FIG. 21, a slope of the $k_{off}$ curve is less steep for the peptide with NAA Phe than for the peptide with NAA Tyr, thus leading to the improved KD. Similarly, the dissociation rate of V1 is significantly slower than that for the wild-type protein. From the dissociation curves, the $k_{off}$ was calculated for each protein with each NAA bearing peptide and the data is displayed in Table 5. The dissociation rate for variant 1 has slowed 9.4-fold over the wild-type protein for Phe; while, the variant 2 dissociation rates have slowed 27.9 and 51.3-fold over wild-type for Phe and Trp, respectively.

TABLE 5

| $K_{OFF}$ (SEC$^{-1}$) | | | |
|---|---|---|---|
| VARIANT | Phe | Trp | Tyr |
| WT | 0.93 | 1.32 | 1.16 |
| V1 | 0.1 | 0.76 | 0.5 |
| V2 | 0.03 | 0.03 | 0.05 |

In addition to advancing the field of proteomics, rapid protein or peptide sequencing facilitates protein engineering by eliminating the conventional maintenance of a genotype-phenotype linkage, as is fulfilled by using yeast or phage display. Similarly, in combinatorial peptide drug library screening, the ability to sequence peptides eliminates conventional barcoding. Currently, there is no single molecule protein sequencing technology available. For example, FRET pairs are being used to tag residues and detect amino acids in a technique called "single-molecule peptide fingerprinting" that can be applied when the peptide is translocated through the Clp protease molecular machinery attached to a surface. In an alternative approach, the ionic current fluctuation pattern within nanopores can be detected to directly discriminate between different groups of amino acids. Engineered nanopores can also be used as a potential way to cleave a single amino acid, and, combined with mass spectrometry, identify that amino acid. Additionally, it has been proposed that partial sequencing, or fluorosequencing can be accomplished by immobilizing a peptide to a surface such that single-molecule fluorescence can be measured. In this measurement modality, the fluorescence detection can be accomplished by either chemically modifying the amino acids based on their unique side chain chemistry, or by using a fluorescently labeled amino acid binding reagent. The approach of chemical modification has been successfully employed to detect cysteine and lysine residues. The specificity and affinity requirements of a potential NAAB is dependent on the limits of detection of the technology being employed, however some groups are exploring the theoretical limitations to which lower affinity NAABs can still potentially be useful reagents.

This work shows that NAABs that are enhanced in specificity and affinity for some NAAs can indeed be engineered from ClpS proteins, which natively recognize some NAAs, using directed evolution and yeast-based FACS screening methods. The initial directed evolution design targeted all of the ClpS residues in a random fashion, rather than relying on structural insights into the exact location of the binding pocket. However, many of the residues that were ultimately found to be mutated were indeed in or near the binding pocket and recapitulate properties that could perhaps have been rationally designed from critical assessment of the crystal structures available in the literature. The strategy of targeting the residues that frequently occurred after the first set of selections with a more in depth, focused library testing each of the 20 residues at these positions resulted in more hits during subsequent rounds of selection. However, there is still the possibility of evolving these proteins further, for enhanced selectivity and affinity for the Trp or Phe NAAs, or for other amino acid targets such as Tyr and Leu, by combining the mutations found in this work with those that may be found among the different homologs in the literature with known differences in specificity. Additionally, in a peptide sequencing context, ideally the second amino acid must not significantly affect the binding of the NAAB or false positives could occur. The finalized NAAB reagents will ultimately need to be characterized against a panel of peptides to ensure that the neighboring sequence does not affect the sequencing fidelity, as has been done for the some of the wild-type ClpS proteins. Although there is a significant amount of characterization of this family of proteins in the literature, it has previously been studied in ways which focus on the properties of ClpS that contribute to the selection of substrates for degradation within a cell. As with any engineering effort, one must strive to understand as much as possible about a system in order to engineer it to perform a new or different task. From the standpoint of using ClpS homologs as potential tools or binding reagents, the criteria and attributes by which protein engineers assess this protein are beginning to evolve. For instance, assessing the ability of ClpS to bind non-standard amino acids that it would not normally encounter in nature contributed to the use of the protein to detect non-standard amino acid incorporation. In this Example, the finding that the ClpS mutants with higher NAA target affinities are driven by reduced rates of dissociation (koff) is encouraging from a binding reagent standpoint. It poises these mutant proteins as binding reagents for NAA detection in fluorescence based sequencing technologies as the slowed rate of dissociation provides a longer residence time for fluorescence-based imaging of the NAAB.

SPR experiments were performed with the peptide affixed to a surface and showed that ClpS binds peptides in a surface-attached configuration (also referred herein as anchoring). The yeast display system provides efficient activity in vitro in the surface adhered peptide context, fluorescent labeling, and stability to the length of incubation times, temperatures, and buffer conditions involved in sequencing detection.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A binder complex for selectively identifying an amino acid, the binder complex comprising:

an amino acid-specific binder; and an adjunct attached to the amino acid-specific binder, wherein the amino acid-specific binder binds selectively to a binding amino acid, and the amino acid-specific binder comprises an amino acid sequence that comprises:

(Sequence ID No. 10)
NLEKIKKLRNVIKEIKKDNIKEADEHEKKEREKETSAWKVILYNDDIHK
FSYVTDVIVKVVGQISKAKAHTITVEAHSTGQALILSTWKSKAEKYCQE
LQQNGLTVSIIHESQLKDKQKK.

2. The binder complex of claim 1, wherein the adjunct comprises a taggant, a protein, a substrate, or a chemical modifier.

3. The binder complex of claim 2, wherein the taggant comprises:

a fluorescent moiety, an electrochemical moiety, or a combination comprising at least one of the foregoing moieties, and the taggant produces a taggant signal in response to receiving a stimulus.

4. A process for selectively identifying an N-terminal amino acid, the process comprising:

providing an analyte comprising a protein, a peptide, an amino acid, or a combination comprising at least one of foregoing;

contacting a C-terminal end of the analyte with an anchor;

anchoring the C-terminal end to the anchor to form an anchored analyte;

contacting an N-terminal amino acid of the anchored analyte with a binder complex, the binder complex comprising:

an amino acid-specific binder; and a taggant attached to the amino acid-specific binder;

selectively binding the amino acid-specific binder of the binder complex to the N-terminal amino acid of the anchored analyte when the N-terminal amino acid comprises a binding amino acid to form a tagged complex;

subjecting the taggant of the tagged complex to a stimulus;

producing, by the taggant of the tagged complex, a taggant signal in response to the stimulus;

detecting the taggant signal; and identifying the N-terminal amino acid based on the taggant signal, wherein the amino acid-specific binder binds selectively to the binding amino acid, and the amino acid-specific binder comprises an amino acid sequence comprising:

(Sequence ID No. 10)
NLEKIKKLRNVIKEIKKDNIKEADEHEKKEREKETSAWKVILYNDDIHK

FSYVTDVIVKVVGQISKAKAHTITVEAHSTGQALILSTWKSKAEKYCQE

LQQNGLTVSIIHESQLKDKQKK.

5. The process of claim 4, further comprising:

removing the N-terminal amino acid from the anchored analyte so that a penultimate residue becomes the N-terminal amino acid of the anchored analyte;

contacting the N-terminal amino acid of the anchored analyte with the binder complex;

selectively binding the amino acid-specific binder of the binder complex to the N-terminal amino acid of the anchored analyte when the N-terminal amino acid is the binding amino acid to form the tagged complex;

subjecting the taggant of the tagged complex to the stimulus;

producing, by the taggant of the tagged complex, the taggant signal in response to the stimulus;

detecting the taggant signal; and identifying the N-terminal amino acid based on the taggant signal.

6. The process of claim 4, further comprising:

converting the N-terminal amino acid to an inert residue;

converting a penultimate residue to be the N-terminal amino acid when the inert residue is produced;

contacting the N-terminal amino acid of the anchored analyte with the binder complex;

selectively binding the amino acid-specific binder of the binder complex to the N-terminal amino acid of the anchored analyte when the N-terminal amino acid is the binding amino acid to form the tagged complex;

subjecting the taggant of the tagged complex to the stimulus;

producing, by the taggant of the tagged complex, the taggant signal in response to the stimulus;

detecting the taggant signal; and identifying the N-terminal amino acid based on the taggant signal.

7. The process of claim 6, wherein converting the N-terminal amino acid to the inert residue comprises chemically changing the N-terminal amino acid prior to producing the inert residue.

8. The process of claim 7, wherein chemically changing the N-terminal amino acid prior to producing the inert residue comprises phosphorylating a free amine of the N-terminal amino acid.

9. A process for selectively isolating an analyte, the process comprising:

contacting an amino acid-specific binder with an analyte comprising a protein, a peptide, an amino acid, or a combination comprising at least one of foregoing;

selectively binding the amino acid-specific binder to the N-terminal amino acid of the analyte when the N-terminal amino acid comprises a binding amino acid to form an isolation complex;

separating the isolation complex from a fluid in which the isolation complex is disposed to selectively isolating the analyte, wherein the amino acid-specific binder binds selectively to the binding amino acid, and the amino acid-specific binder comprises an amino acid sequence comprising:

(Sequence ID No. 10)
NLEKIKKLRNVIKEIKKDNIKEADEHEKKEREKETSAWKVILYNDDIHK

FSYVTDVIVKVVGQISKAKAHTITVEAHSTGQALILSTWKSKAEKYCQE

LQQNGLTVSIIHESQLKDKQKK.

10. The process of claim 9, wherein separating the isolation complex from the fluid in which the isolation complex is disposed comprises:

separating the isolation complex based on a size of the isolation complex relative to a size of other constituents in the fluid;

precipitating the isolation complex from the fluid;

centrifuging; or a combination comprising at least one of the foregoing separations.

11. The process of claim 9, wherein the amino acid-specific binder is a member of a binder complex.

12. The process of claim 11, wherein the binder complex comprises:

the amino acid-specific binder; and an adjunct attached to the amino acid-specific binder.

13. The process of claim 12, wherein the adjunct comprises a taggant, a protein, a substrate, or a chemical modifier.

14. The process of claim 13, wherein the taggant comprises:

a fluorescent moiety, an electrochemical moiety, or a combination comprising at least one of the foregoing moieties, and the taggant produces a taggant signal in response to receiving a stimulus.

15. The process of claim 14, further comprising:
subjecting the taggant of the isolation complex to a stimulus;
producing, by the taggant of the isolation complex, a taggant signal in response to the stimulus;
detecting the taggant signal; and
identifying the N-terminal amino acid based on the taggant signal.

16. The process of claim 14, wherein the stimulus comprises a photon; and
the taggant signal comprises fluorescence emitted from the taggant.

17. The process of claim 9, further comprising:
contacting the amino acid-specific binder with an adjunct to form a binder complex prior to contacting the amino acid-specific binder with the analyte.

* * * * *